United States Patent
Borowski et al.

(10) Patent No.: US 9,447,136 B2
(45) Date of Patent: Sep. 20, 2016

(54) SEMISYNTHETIC DERIVATIVES OF NYSTATIN $A_1$

(71) Applicant: BLIRT S.A., Gdansk (PL)

(72) Inventors: Edward Borowski, Gdasnk (PL); Natalia Salewska, Gdynia (PL); Joanna Boros-Majewska, Gdansk (PL); Maria Milewska, Gdansk (PL); Malgorzata Wysocka, Gdansk (PL); Slawomir Milewski, Gdansk (PL); Andrzej Skladanowski, Gdansk (PL); Adam Treder, Przyjazn (PL); Ewa Sadowska, Gdansk (PL); Izabela Chabowska, Bytow (PL)

(73) Assignee: BLIRT S.A., Gdansk (PL)

( * ) Notice: Subject to any disclaimer, the term of this patent is extended or adjusted under 35 U.S.C. 154(b) by 0 days.

(21) Appl. No.: 14/383,530

(22) PCT Filed: Mar. 7, 2013

(86) PCT No.: PCT/EP2013/054621
§ 371 (c)(1),
(2) Date: Sep. 5, 2014

(87) PCT Pub. No.: WO2013/132014
PCT Pub. Date: Sep. 12, 2013

(65) Prior Publication Data
US 2015/0045316 A1      Feb. 12, 2015

(30) Foreign Application Priority Data
Mar. 9, 2012   (PL) .......................................... 398390

(51) Int. Cl.
*C07H 17/08*    (2006.01)

(52) U.S. Cl.
CPC ..................... *C07H 17/08* (2013.01)

(58) Field of Classification Search
CPC ........................................................ C07H 17/08
USPC .............................................. 514/31; 536/6.5
See application file for complete search history.

(56) References Cited

U.S. PATENT DOCUMENTS

| | | | |
|---|---|---|---|
| 3,244,590 A | 4/1966 | Schaffner et al. | |
| 3,780,173 A | 12/1973 | Bruzzese et al. | |
| 4,144,328 A | 3/1979 | Vainshtein et al. | |
| 4,195,172 A * | 3/1980 | Falkowski | C07H 17/08 536/6.5 |
| 4,272,525 A | 6/1981 | Wright | |
| 4,396,610 A | 8/1983 | Witzke | |
| 5,942,495 A * | 8/1999 | Borowski | C07H 17/08 514/31 |
| 5,981,721 A | 11/1999 | Mohan | |
| 6,413,537 B1 | 7/2002 | Kwon et al. | |
| 6,562,796 B2 * | 5/2003 | Baldwin | C07H 17/08 514/31 |
| 6,664,241 B2 | 12/2003 | Chang et al. | |
| 2002/0094961 A1 | 7/2002 | Baldwin et al. | |

FOREIGN PATENT DOCUMENTS

| | | |
|---|---|---|
| DE | 2706156 | 8/1978 |
| EP | 0375222 B1 | 6/1990 |
| EP | 0375223 A2 | 6/1990 |
| EP | 2 174 944 | 4/2010 |
| GB | 1387187 | 3/1975 |
| GB | 2027698 | 2/1980 |
| PL | 82224 B | 10/1975 |
| PL | 100966 B | 3/1979 |
| PL | 122884 B | 8/1982 |
| PL | 142848 | 12/1987 |
| PL | 199213 B1 | 8/2001 |
| PL | 210774 B1 | 12/2007 |
| PL | 199213 B | 8/2008 |
| WO | WO 93/17034 A1 | 9/1993 |

(Continued)

OTHER PUBLICATIONS

Zerbib et al, Rapid Commun. Mass Spectrom. Aug. 15, 2011, 25, 2141-48.*

(Continued)

*Primary Examiner* — Ganapathy Krishnan
(74) *Attorney, Agent, or Firm* — Knobbe, Martens, Olson & Bear LLP

(57) ABSTRACT

The invention provides semisynthetic derivatives of Nystatin $A_1$, water soluble salts and complexes, pharmaceutical compositions and plant protection products comprising the derivatives and their use, as antifungal antibiotics (Formula 1a).

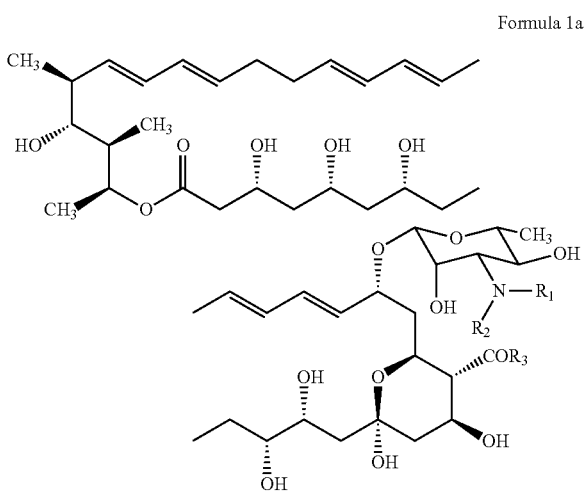

Formula 1a

18 Claims, No Drawings

(56) References Cited

FOREIGN PATENT DOCUMENTS

| WO | WO 96/35701 A1 | 11/1996 |
|---|---|---|
| WO | WO 99/51274 | 10/1999 |
| WO | WO 01/51061 A1 | 7/2001 |
| WO | WO 01/68102 | 9/2001 |
| WO | WO 01/91758 A1 | 12/2001 |
| WO | WO 2007/096137 | 8/2007 |
| WO | WO 2007/096137 A1 | 8/2007 |

OTHER PUBLICATIONS

Bonner D. P. et al., Polyene macrolide derivatives. III Biological properties of polyene macrolide ester salts, J. Antibiot., 25(4)261-262,1972.

Borgos S. E. F. et al., Probing the structure-function relationship of polyene macrolides: engineered biosynthesis of soluble nystatin analogues, J. Med. Chem., 49(8):2431-2439, 2006.

Borowski E. et al., The complete structure of the polyene macrolide antibiotic nystatin $A_1$, Tetrahedron Lett., 8:685-690, 1971.

Bruzzese T. et al., Partricin methyl ester, a semisynthetic polyene antibiotic, Experientia 28(12):1515-1516, Dec. 15, 1972.

Bruzzese T. et al., Synthesis and biological properties of alkyl esters of polyene antibiotics, J. Pharm. Sci. 64(3):462-463,March 975.

Czerwiński A., N-dimethylaminoacyl derivatives of polyene macrolide antibiotics, The Journal of Antibiotics, 39 (7):1025-1027, Jul. 1986.

Demain A. L. et al., Microbial drug discovery: 80 years of progress, J. Antibiot., 62:5-16, 2009.

Enoch D. A. et al., Invasive fungal infections: a review of epidemiology and management options, J. Med. Microbiol., 55:809-818, 2006.

Falkowski L. et al., Methyl esters of trimethyl-ammonium derivatives of polyene macrolide antibiotics, J. of Antibiotics. 32(10):1080-1081, Oct. 1979.

Falkowski L. et al., The preparation of n-glycosyl derivatives of polyene macrolide antibiotics and their comparative antifungal activities, Acta Polon. Pharm., 37(5):517-520, 1980.

Falkowski L. et al., The preparation of methyl esters of trimethylammonium derivatives of polyenes macrolide antibiotics and their biological properties, Acta Polon. Pharm., 37(6):631-634, 1980.

Falkowski L. et al., N-glocosyl derivatives of polyene macrolide antibiotics, J. Antibiot., 28(3):244-245, Mar. 1975.

Falkowski L. et al., The structure of n-glycosyl derivatives of polyene macrolide antibiotics. The reaction of nystatin with $_D$-glucose, Polish J. Chem., 56:123-130, Jan. 1982.

Franz R. et al., Multiple molecular mechanisms contribute to a stepwise development of fluconazole resistance in clinical candida albicans strains, Antimicrob Agents Chemother., 42(12):3065-3072, Dec. 1998.

Franz et al., Molecular aspects of fluconazole resistance development in Candida albicans, Mycoses, 42:453-458,1999.

Fridkin S. K., Candidemia is costly-plain and simple, Clin. Infect. Dis., 41:1240-1241, Nov. 1, 2005.

Grzybowska et al, Hydrazides—a novel type of derivatives of polyene macrolide antifungal antibiotics, J. Antibiot.,43(7):907-908, Jul. 1990.

Hazen et al., Fungicidin, an antibiotic produced by a soil actinomycete, Proc. Soc. Exptl. Biol., 76:93-97, 1951.

Hazen et al., Two antifungal agents produced by a soil actinomyete, Science, 112, 112, 1950.

Kontoyiannis et al., Antifungal drug resistance of pathogenic fungi, Lancet, 359:1135-1144, Mar. 30, 2002.

Nucii N. et al., Emerging fungal diseases, Clin. Infect Dis., 41:521-526, Aug. 15, 2005.

Paquet et al., Significant improvement of antifungal activity of polyene macrolides by bisalkylation of the mycosamine, Org. Lett., 8(9):1807-1809, 2006.

Patterson, Advances and challenges in management of invasive mycoses, Lancet, 366:1013-1025, Sep. 17, 2005.

Pawlak et al., The structure of Nystatin $A_2$, Polish J. Chem., 79:1673-1679, 2005.

Petersen, Intramolecular fluorescence energy transfer in nitrobenzoxadiazole derivatives of polyene antibiotics, Can. J. Chem. 63 (1):77-85, 1985.

Pfaller M. A. et al., Epidemiology of invasive candidiasis: a persistent public health problem, Clin. Microbiol. Rev. 20(1):133-163, Jan. 2007.

Porowska et al., Composition of polifungin, a new antifungal agent, Rec. Trav. Chem., 91:780-784, 1971.

Ramirez F. et al., Differential effects on energy transduction processes by fluorescamine derivatives in rat liver mitochondria, Biochem. 19(9):1928-1933, 1980.

Sanglard D. Resistance of human fungal pathogens to antifungal drugs, Curr. Opinion Microbiol., 5:379-385, 2002.

Schaffner et al., Biologically active N-Acyl derivatives of polyene macrolide antifungal antibiotics, Antibiot. Chemother., 11(11):724-732, 1961.

Schaffner, Chapter 12. Polyene macrolides in clinical practice: pharmacology and adverse and other effects, in Macrolide Antibiotics: Chemistry, Biology, and Practice, Academic Press. Inc., Orlando, pp. 457-507, 1984.

Schaffner et al., Polyene macrolide derivatives. I: N-acylation and esterification preactions with amphotericin B, J. Antibiot., 25(4):256-258, Apr. 1972.

Semis R. et al., Activity of an intralipid formulation of nystatin in murine systemic candidiasis, J. Antimicr. Ag., 38:336-340, 2011.

Semis R. et al., Phamacokinetics, tissue distribution and immunomodulatory effect of intralipid formulation of nystatin in mice, J. Antimicrob. Chemother., 67:1716-1721, 2012.

Semis R. et al., Mechanism of activity and toxicity of nystatin-intralipid, Med. Mycol., 51:422-431, May 2013.

Semis R. et al., Nystatin-intralipid preparation: characterization and in vitro activity against yeasts and molds, Mycopathologia, 169:333-241, 2010.

Silva L. et al., Solution conformation of a nitrobenzoxadiazole derivative of the polyene antibiotic nystatin: a FRET study, J. Photochem. Photobiol. B. Biol., 72:17-26, 2003.

Singh N., Invasive aspergillosis in organ transplant recipients: new issues in epidemiologic characteristics, diagnosis, and management, Med. Mycol. Suppl 1, 43:S267-S270, 2005.

Ślisz et al., Studies of the effects of antifungal cationic derivatives of amphotericin B on human erythrocytes, J Antibiot., 57(10):669-678, Oct. 2004.

Ślisz et al., The mechanism of overcoming multidrug resistance (MDR) of fungi by amphotericin B and its derivatives, J Antibiot., 60(7):436-446, 2007.

Soloviera S. E. et al., Chemical modification of antifungal polyene macrolide antibiotics, Rus. Chem. Rev. 80(2):103-126, 2011.

Sowinski P. et al., The structure of amphotericin A: II. The complete structure of the antibiotic, J. Antibiot., 38(2)175-180, Feb. 1985.

Stefanska B. et al. A new method of preparation of polyene macrolide antibiotics esters, Acta Poloniae Pharmaceutica. 40(2): 171-174, 1983.

Stefańska B. et al., Enamine and amidine derivatives of polyene macrolide antibiotics, Acta Polon. Pharm., XLV(1):71-76, 1988.

Thomas A. H. et al., The heterogeneous composition of pharmaceutical-grade nystatin, The Analyst, 107(1277):849-854, Aug. 1982.

Thomas A. H. et al., Identification and determination of the qualitative composition of nystatin using thin-layer chromatography and high-performance liquid chromatography, J. Chemother., 216:367-373, 1981.

Tsao S. et al., Relative contributions of the candida albicans ABC transporters Cdr1p and Cdr2p to clinical azole resistance, Antimicrobial Agents and Chemotherapy, 53(4):1344-1352, Apr. 2009.

Wakiec R. et al., Voriconazole and multidrug resistance in candida albicans, Mycoses, 50:109-115, 2007.

Yu et al., Organofluorine derivatives of nystatin, Pharmac. J., 32(2):109-110, 1998.

Zerbib C. et al. One-pot synthesis of a new antifungal polymerisable monomer and its characterization by coordination-ion spray mass spectrometry, Rapid Comm. in Mass Spec. 25(15):2141-2148, 2011.

(56) References Cited

OTHER PUBLICATIONS

Zieliński J. et al., The structure of a novel sugar component of polyene macrolide antibiotics: 2,6-dideoxy-L-ribohexopyranose, J. Antibiot., 32(6):565-568, Jun. 1979.
Zieliński J. et al., The structure of nystatin $A_3$, a component of nystatin complex, J. Antibiot., 41(9):1289-1291, Sep. 1988.
International Search Report and Written Opinion dated Aug. 26, 2013 in PCT/EP2013/054621.
Belakhov V.V. et al. Khimiko-Farmatsevicheskii Zhurnal. 25(11)45-48, 1991.
Bronin G.O. et al., Pediatryia, 4:31-37, 2004.
Kushnir V.N. et al., Synthesis and antimicrobial activity on n-cinnamoyl and β-substituted N-acryloyl derivatives of urea, Khim. Farm. Zh., 11(1):45-50, Jan. 1977.
Milewska, Maria J. et al., N-substituted derivatives of nystatin of improved selective toxicity are active against multidrug-resistant yeast, Sep. 23-27, 2010, p. 61; P13, 28th Small Meeting on Yeast Transport and Energetics: (SMYTE), Abstract Book Poster Session, New Delhi, India.
The Patent Office of the Republic of Poland, Search Report, Jul. 31, 2012, Warszawa, Poland.
The Patent Office of the Republic of Poland, Search Report, Oct. 18, 2012, Warszawa, Poland.

* cited by examiner

SEMISYNTHETIC DERIVATIVES OF NYSTATIN A$_1$

The invention concerns water soluble and reduced toxicity, sterically hindered derivatives of the antifungal antibiotic, Nystatin A$_1$ which contain bulky fragments on the substituent linked to the amino group of the antibiotic, which may cause steric hindering effects, as well as esters and amides of such derivatives and their salts with acids or bases or formulations containing complexing compounds, as water-soluble forms, and their use for the production of antifungal preparations primarily for medical and veterinary needs and for plant protection, as well as for other applications like overcoming the fungal invasion in buildings.

BACKGROUND TO THE INVENTION

Antibiotic Nystatin A$_1$ is the main component of antibiotic complex Nystatin, a group of tetraeno-diene polyene macrolides produced by *Streptomyces noursei* (E. L. Hazen, R. Brown, Science 112, 112, 1950; E. L. Hazen, R. Brown, Proc. Soc. Exptl. Biol., 76, 93, 1951; A. H. Thomas and in., J. Chemother., 216, 367, 1981; A. H. Thomas et al., Analyst 107, 849, 1982) which in addition to Nystatin A$_1$ (Borowski et al., Tetrahedron Lett. 8, 685, 1971) also contains Nystatin A$_2$ (J. Pawlak et al., Polish J. Chem. 79, 1673, 2005) and Nystatin A$_3$ (J. Zielinski et al., J. Antibiot. 41, 1289, 1988). Nystatin A$_1$ is currently commercially available in acceptably pure form, manufactured by Bristol-Myers-Squibb in USA, as well as by other companies. Nystatin A$_1$ and other components of antibiotic complex Nystatins are also produced by *Streptomyces noursei* var. *Polyfungini* named polyfungin (N. Porowska et al., Rec. Tray. Chem. 91, 780, 1971). This complex contains additionally a new component called polyfungin B (Zielinski et al., J. Antibiot. 32, 565, 1979). Among tetraeno-diene polyene macrolides, well identified compound is also Amphotericin A (P. Sowinski et al., J. Antibiot. 38, 175, 1985), produced together with Amphotericin B by *Streptomyces nodosus*. According to our invention, spatially hindered derivatives of Nystatin A$_1$ and process of their preparation also apply to the other above-mentioned tetraeno-dienes.

Chemotherapy of fungal infections is one of the most difficult and not yet successfully solved problems in modern medicine. This is a consequence of the fact that both, pathogenic fungal organisms, and the humans are eukaryotic organisms and this is the reason of essential difficulties in developing the selectively acting drugs with low toxicity for the patients. This difficulty has been omitted in the treatment of topical fungal infections. This includes such areas of clinical mycology as gynecology, dermatology, gastroenterology, pulmomology, urology and ophthalmology, where the problem of compounds toxicity occurs to be less dramatic (C. P. Schaffner, in Macrolide antibiotics, S. Omura (ed.), Academic Press. Inc., Orlando, p. 457, 1984). The most popular drugs from polyene group for such treatment are Nystatin, Pimaricin and Amphotericin B, which due to the lack of resorption in oral administration are practically non-toxic. However, invasive mycoses concerning the infection of internal organs and fungemia are still problems far from successful solution. Current epidemiological statistics concerning the mortality in such types of illnesses are not satisfactory (M. A. Pfaller, D. J. Diekem, Clin. Microbiol. Rev. 20, 133, 2007; T. F. Patterson, Lancet 366, 1013, 2005; S. K Fridkin, Clin. Infect. Dis. 41, 240, 2005). Especially dangerous are invasive candidoses and aspergilloses and infections caused by certain other fungal pathogenes. In the case of invasive candidosis the mortality is in the range 30-70%, aspergillosis more than 50%, the frequency of invasive mycoses in oncology/hematology is approximately 50%, in the case of mycoses of children with leukemia is 29-39% (S. E. Soloviera et al., Rus. Chem. Rev. 80, 103, 2011: A. L. Demain, S. Sanchez, J. Antibiot., 62, 5, 2009; G. O. Bronin et al., Pediatryia 4, 31, 2004). Over 90% of HIV-positive patients suffer from mycoses, while pneumonia caused by *Pneumocystis carinii* is the main reason of death in patients with AIDS. Systemic mycoses are common reason of death in adult patients with leukemia. *Candida* spp., in regard to frequency of incidences, are the fourth etiological factor of hospital infections and is a cause of 8-11% of all general infection with mortality up to 40%. The frequency of fungal infections in patients after organ transplants is in the range 5-40% depending on the type of organ transplanted. Invasive aspergilosis of lungs is main reason of patients death after transplant of bone marrow. Blastomycosis, histoplasmosis and coccidiomycosis are endemic mycoses with high frequency of appearance in many regions of the world.

The unfavourable situation in the clinical mycology since over 20 years is constantly getting worse for several reasons. One of them is steady increase of infections caused by species of fungal microorganisms previously being non-pathogenic (D. A. Enoch et al., J. Med. Microbiol. 55, 809, 2006; N. Nucii, K. A. Man, Clin. Infect Dis. 41, 521, 2005). The increase of fungal infections is also caused by the use of antibacterial chemotherapeutical agents with broad spectrum and by the use of steroids, and above all by decreasing the immune system activity in an increasing number of patients, connected with the development of transplantology, which required the use of immunosuppressive drugs, and also with the increase of cancer cases and thus usage of immunosuppressive cytostatics (N. Siugh, Med. Mycol. 43, suppl. 1, 267, 2005; A. L. Demain, S. Sanchez, J. Antibiot. 62, 5, 2009).

Especially alarming is the steady decrease of therapeutic values of currently available antifungal chemotherapeutics used for the treatment of systemic infections, as a result of the rapid development of resistance of pathogenic fungal strains (D. Sanglard, Curr. Opinion Microbiol. 5, 378, 2002; D. P. Kontoyiannis, R. E. Lewis, Lancet 359, 1135, 2002). The most dangerous type of fungal resistance is the multi-drug resistance (MDR), which affects antifunagals activity towards systemic as well as topical administration. The MDR strains overexpress transporter proteins which export a drug from the cells, thus not allowing to retain in fungal cells its therapeutic concentration.

Enzyme inhibitor, 5-fluorocytosine, often used in combination with Amphotericin B to increase its uptake by membrane permeabilisation, as an antimetabolite avoids the exporting activity of MDR transporting proteins, but enhances the development of specific type of resistance mainly by the loss of cytosine permease and deaminase. Particularly clinically valuable fungicides of "azoles" group, mostly triazoles, such as flucanazole, voriconazole, posaconazole and others, are partially susceptible to their removal from the cells by MDR exporting proteins (R. Franz et al., Antimicrob. Ag. Chemother., 42, 3065, 1998; R. Wakiec et al., Mycoses, 50, 109, 2007). However, being the inhibitors of lanosterol demethylase, interacting with the enzyme, also induce the changes in the structure of enzymatic protein leading to the loss of inhibitory activity of these compounds. Valuable and very promising fungicide caspofungin, although with narrow antifungal spectrum but with excellent selectivity, as inhibitor of β-D-glucan synthase, interacts with the enzyme, which unfortunately leads to the induction of changes in the structure of enzyme protein and in consequence the loss of inhibitory activity of compound. The reports on growing resistance to the action of this drug are starting to be published. Therefore, concerning the MDR problem, there practically remains only one effective group of fungicides, polyene macrolides, which do not induce the development of resistant strains. These antibiotics as not being the substrates of MDR exporting proteins, retain full activity against multidrug resistant strains (M. Slisz i in., J Antibiot. 60, 436, 2007). Although there is data on the appearance of strains with reduced sensitivity to these antibiotics, as a result of certain changes in the lipid composition of cytoplasmic membrane, but these changes are rather phenotypic and regressing after discontinued contact with the drug.

Presented situation in clinical mycology points to the necessity of further search for antifungal drugs. One of the intensively developing research projects concerned study on the modifications of polyene macrolides aimed at removing of their main shortcomings, which are high toxicity and lack of water solubility of native compounds. However, until now none of the products of this antibiotics modification have been introduced to clinical practice. The only practical progress in this area was the introduction to clinical use of Amphotericin B complexes with lipids or liposomal formulations as Abalcet®, Amphotec® and AmBisome®. However, these formulations of Amphotericin B are only a little less toxic in comparison to the native antibiotic.

Due to the high toxicity of Amphotericin B, as well as its very high cost, the attention has been drawn by another clinical antibiotic from polyenes group, Nystatin, so far used only topically. This antibiotic exhibits all advantageous features of that type of compounds such as: broad antifungal spectrum, fungicidal effect, high antifungal activity, lack of induction of resistance and lack of interaction with overexpressed protein transporters in multidrug resistant strains (MDR). Furthermore, Nystatin is much cheaper than Amphotericin B. Studies have been undertaken on the application of Nystatin also in the treatment of systemic fungal infections, using soluble lipidic and lyposomal formulations (R. Semis et al., Mycopathologia, 169, 333, 2010; R. Semis et al., J. Antimicr. Ag., 38, 336, 2011; R. Semis et al., J. Antimicrob. Chemother., 67, 1716, 2012; R. Semis et al., Med. Mycol. Month Early on line 1, 2012).

The studies on chemical modifications of Nystatin have been also carried out. Earlier obtained Nystatin $A_1$ derivatives, are compounds with the modified amino group of the mycosamine moiety and also the carboxyl group of aglycone. The attempts to modify compounds by genetic manipulations of antibiotic-producing organism have also been performed. Chemical modifications of Nystatin $A_1$ have been intended to improve the solubility and to reduce toxicity of the compounds. However, no significant progress has been achieved in this matter, because no theoretical background for the rational modifications has been worked out. The synthesis of derivatives had accidental character and were based rather on random screening.

The prior art on Nystatin $A_1$ derivatives includes 1) derivatives at amino group; 2) derivatives at carboxyl group; 3) double derivatives including amino and carboxyl group; 4) analogues with genetically modified aglycone fragment.

Among the derivatives at amino group many N-acyl derivatives have been synthesized. There are simple derivatives (U.S. Pat. No. 3,244,590; C. P. Schaffner, E. Borowski, Antibiot. Chemother. 11, 724, 1961), more complicated ones (L. Silva et al., J. Photochem. Photobiol. B. Biol. 72, 17, 2003), compounds including fluoroorganic derivatives (Yu. Shenin et al., Pharmac. J. 32, 109, 1996), amino acyl derivatives (A. Czerwiński., J. Antibiot. 39, 1025, 1986; Polish Patent 142847). Other derivatives at amino group comprise guanidine derivative (U.S. Pat. No. 4,396,610), N-enamine and amidine derivatives (Stefańska et al., Acta Polon. Pharm., XLV, 71, 1988; Polish Patent 120111), N-trialkylsilyl derivatives (V. V. Balakhov et al., Khim. Farm. Zh. 11, 45, 1977) and Schiff bases (V. V. Balakhov et al., Khim. Farm. Zh. 11, 45, 1977). A large group constitutes N-alkyl derivatives. These are N-alkylhydrofosforyl derivatives (V. V. Belakhov et al., Khim. Farm. Zh. 25, 45, 1991), N,N,N-trimethyl derivative (U.S. Pat. No. 4,144,328), products of reductive N-alkylation (V. Paquet, E. M. Carreira, Org. Lett. 8, 1807, 2006; U.S. Pat. No. 6,664,241 B2). Particular attention is drawn to N-alkyl derivatives which are N-glycosyl products of Amadori reaction rearrangement (L. Falkowski et al., J. Antibiot. 28, 244, 1975; L. Falkowski et al., Acta Polon. Pharm. 37, 517, 1980; L. Falkowski et al., Polish J. Chem. 56, 123, 1982; Polish Patent 82224; U.S. Pat. No. 6,664,241 B2) and their water-soluble salts with N-methyl-D-glucamine (U.S. Pat. No. 4,195,172).

Nystatin $A_1$ derivatives with modified carboxyl group include a number of compounds. These are esters (T. Bruzzesse et al., Experientia 28, 1515, 1972; T. Bruzzesse et al., J. Pharm. Sci. 64, 462, 1975; U.S. Pat. No. 3,780,173; P. Schaffner, W. Mechlinski, J. Antibiot. 25, 259, 1972; D. P. Bonner et al., J. Antibiot. 25, 261, 1972; B. Stefańska et al., Acta Polon. Pharm. 40, 71, 1983; U.S. Pat. No. 5,981,721), hydrazides (J. Grzybowska, E. Borowski J. Antibiot. 43, 907, 1990) and amides (Polish Patent 138831; U.S. Pat. No. 6,664,241 B2), as well their soluble salts (Polish Patent 138831).

There are also known Nystatin $A_1$ derivatives modified in both amino and carboxyl groups of the antibiotic. These compounds combine above described types of chemical modification at both groups. They include the methyl ester of N,N,N-trimethyl derivative (L. Falkowski et al., J. Antibiot. 32, 1080, 1979; L. Falkowski et al., Acta Polon. Pharm., 37, 631, 1980; Polish Patent 122884), methyl esters of N-enamine and amidine derivatives (Polish Patent 120035), esters of guanidine derivatives (U.S. Pat. No. 4,396,610), methyl ester of N-fructosyl-N-methyl Nystatin $A_1$ (Polish patent 199213), esters of glycosyl derivatives (U.S. Pat. No. 6,562,796 B2), methyl esters of aminoacyl derivatives (Polish Patent 142848) and amides of N-mono and di-alkyl, as well of N-glycosyl derivatives.

Efforts have been also made to modify the macrolide ring of Nystatin $A_1$ by the genetic manipulation of *Streptomyces noursei*, which produces this antibiotic. That way two new hydroxyl groups have been introduced to that ring, which slighty increase the hydrophilicity of the molecule and thus improve its solubility in water (S. F. E. Borgos et al., J. Med. Chem. 49, 2431, 2006). However, these derivatives cannot be regarded as derivatives of Nystatin $A_1$, but as its analogs. Similarly, other genetic modifications of the antibiotic "producer" also lead to obtaining novel antibiotics and their derivatives, which cannot be classified as a semi-synthetic derivatives of the original native product, Nystatin $A_1$ (International Patent Application PCT/GB2008/002238). Other known Nystatin derivatives are presented in the patent specification WO 01/68102, and in U.S. Pat. No. 6,413,537.

Among above mentioned Nystatin $A_1$ derivatives, there are no compounds which could combine features, particularly important for practical application, such as water solubility and essentially reduced toxicity.

The advantage of new semisynthetic Nystatin $A_1$ derivatives, according to the invention, is that they exhibit low hemotoxicity, which is a common toxicity test for compounds of polyene macrolides group, and form water soluble salts. They also exhibit antifungal activity towards broad spectrum of *Candida* species, filamentous fungi and dermatophytes and against strains with multidrug resistance (MDR) with overexpression of MDR protein transporters MDR1p, as well as Cdr1p and Cdr2p.

Unexpected novelty enabling to obtain according to the invention, advantageous effect of hemotoxicity reduction and water solubility, is introduction to substituents at amino group of Nystatin $A_1$ of bulky moieties, which induce steric hindrance effects. It appeared that such steric hindrance factors decrease lethal permeabilising activity of Nystatin $A_1$ derivatives a greater degree towards mammalian than fungal cells, which increases their selectively of action and essentially reduces the hemotoxicity of these compounds. The presence of a bulky moiety attached to the amino group of Nystatin $A_1$ also disturbs the zwitterionic structure of the antibiotic thus enabling the formation of soluble salts.

Bulky moieties which may give the effect of steric hindrance include ring systems carbo-, as well as heterocyclic, alicyclic and aromatic, bulky substituents as tert-butyl, nitro group, bromine atom and also aliphatic fragments, which, due to their flexibility, can form voluminous conformational structures. The introduction of the steric hindering moieties to the molecule of a biologically active compounds can influence in a different way the affinity to its molecular target, which in the case of Nystatin $A_1$ and its derivatives is ergosterol in fungal cells and cholesterol in mammalian cells. Until now, for Nystatin $A_1$ derivatives, the influence of steric hindrance on the differentiation of lethal effects towards both types of cells has not been known. There is no general rule concerning the influence of steric hindrance of biologically active compounds on their properties. This effect is associated with a defined compound with a specific structure and its conformational dynamics. Nystatin $A_1$ molecule, because of its flexible structure is very dynamic in regard to conformational changes. Effect of steric hindrance of derivatives on their biological properties can be confronted only with other polyene macrolides of the same group which are tetraeno-dienes. In that respect, there is no data available prior to the invention.

SUMMARY OF INVENTION

Accordingly, a first aspect, the invention provides sterically hindered derivatives of Nystatin $A_1$ according to the formula 1:

or a salt or complex thereof;

wherein $R_1$ is independently chosen from a hydrogen atom, optionally substituted alkyl, a succinimidyl derivative, a glycosyl residue, an optionally substituted aminoacyl residue, or an optionally substituted thioureidyl residue;

$R_2$ is a hydrogen atom or a substituent such as defined for $R_1$;

$R_3$ is a hydroxyl group, alkoxyl group or an alkylamino or aminoalkyl derivative.

In certain embodiments, when $R_3$ is hydroxyl, $R_1$ and $R_2$ are not both hydrogen.

Definitions

The term "halogen" or "halo" as used herein means fluorine, chlorine, bromine or iodine.

The term "heteroatom" as used herein refers to one or more of oxygen, sulfur, nitrogen, phosphorus or silicon.

The term "aliphatic" as used herein refers to a straight or branched chain hydrocarbon which is completely saturated or contains one or more units of unsaturation. Thus, aliphatic may be alkyl, alkenyl or alkynyl, preferably having up to 20 carbon atoms, up to 12 carbon atoms or up to 6 carbon atoms.

The terms "bulky" or "spatially expanded", which can be used interchangeably, as used herein refer to a group or moiety which may give the effect of steric hindrance and include ring systems carbo-, as well as heterocyclic, alicyclic and aromatic, bulky substituents as tert-butyl, nitro group, bromine atom and also aliphatic fragments, which, due to their flexibility, can form voluminous conformational structures. In the context of the invention a bulky alkyl may, for example be optionally substituted branched alkyl of 4 or more carbon atoms or an optionally substituted alkyl or alkyl-comprising moiety, also comprising an optionally substituted carbo- or heterocyclic, aminoacyl, thiureidyl or succinimdyl moeity.

The term "alkyl" as used herein refers to a straight or branched chain alkyl group. Preferably, an alkyl group as referred to herein is a $C_1$-$C_{20}$alkyl group, preferably a $C_1$-$C_{12}$alkyl group. More preferably, an alkyl group as referred to herein is a lower alkyl having 1 to 6 carbon atoms.

The term "non-branched", used interchangebly with "simple", as used herein refers to a straight chain alkyl group. Preferably, a simple alkyl group as referred to herein is a lower alkyl having 1 to 6 carbon atoms.

The terms "carbocycle" or "carbocyclic moiety" as used herein refer to a saturated or partially unsaturated mono-, bi- or tri-cyclic group having 3 to 14, preferably 3 to 8 and more preferably 3 to 6, ring carbon atoms or a mono-, bi- or

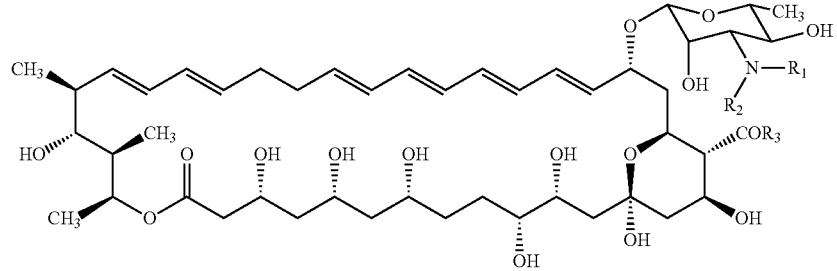

Formula 1 tri-cyclic aromatic ring having 6 to 14, preferably 6 to 10, carbon atoms. A carbocycle is a cycloaliphatic, preferably a "cycloalkyl" which as used herein refers to a fully saturated hydrocarbon cyclic group, or an "aryl". Preferably, a cycloalkyl group is a $C_3$-$C_6$ cycloalkyl group and preferably, an aryl is phenyl or napthyl. Bi- or tri-cyclic groups may contain fused aromatic, saturated and/or partially unsaturated rings.

The terms "heterocycle" or "heterocyclic moiety" as used herein refer to a saturated or partially unsaturated mono-, bi- or tri-cyclic group having 3 to 14, preferably 3 to 10, ring atoms or a mono-, bi- or tri-cyclic aromatic ring having 6 to 14, preferably 6 to 10, ring atoms and having, in addition to carbon ring atoms, one or more ring heteroatoms selected from O, N, P and S (preferably O, N and S). A heterocycle is cycloheteroaliphatic, preferably a "heterocycloalkyl", which as used herein refers to a saturated heterocyclic group, or a "heteroaryl", which refers to a monocyclic or bicyclic aromatic ring system. A heterocycle preferably has 3 to 7 ring atoms or if aromatic, 5 to 10 ring atoms and may contain fused aromatic, satuated and/or partially unsaturated rings. Preferably a heterocycle is piperidine, morpholine, piperazine, pyrrolidine, pyridine or imidazole.

An aliphatic, alkyl, carbocycle, heterocycle, cycloalkyl, aryl, heteroaryl or aminoacyl group as referred to in respect or any of the chemical moeities described herein, may be unsubstituted or may be substituted by one or more substituents independently selected from the group consisting of halo, aliphatic, —OR°, —R°, —SR°, NHR°, —NRO₂, —COR°, —COOR°, —NH₂, —NO₂, —OH, —COOH, —CN, hydroxyalkyl, alkylcarbonyloxy, alkoxycarbonyl, alkylcarbonyl or alkylsulfonylamino, wherein R° is an optionally substituted aliphatic (preferably alkyl), carbocycle (preferably aryl or cycloalkyl) or heterocycle (preferably hereoaryl or heterocycloalkyl) optionally substituted with or with any one or more of substituents independently selected from halo, aliphatic, —OR, —R, —SR, NHR, —NR₂, —COR, —COOOR, —NH₂, —NO₂, —OH, —COOH, —CN, hydroxyalkyl, alkylcarbonyloxy, alkoxycarbonyl, alkylcarbonyl or alkylsulfonylamino, wherein R is as defined for R°, substituted or unsubstituted. Preferred substituents include halo, lower alkyl, alkylamino, —NH₂, NO₂, —OH, —CN, or alkoxycarbonyl.

An alkylamino or aminoalkyl derivative is a moiety comprising an alkylamino or an aminoalkyl moiety, the alkyl portion of which may be optionally substituted with any substituent as described for alkyl above.

The term "alkylamino" as used herein includes "monoalkylamino" and "dialkylamino".

The term "succinimidyl derivative" as used herein refers to a moiety containing a succinimide residue of structure

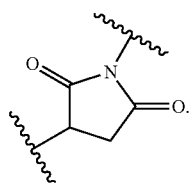 [SMILES: *C1CC(=O)N(*)C1=O]

Preferably, a succinimidyl residue is of structure

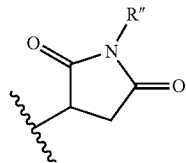

wherein R" is an optionally substituted aliphatic or an optionally substituted carbo- or heterocyclic moiety.

The term "glycosyl" as used herein refers to a cyclic monosaccharide or oligosaccharide. Preferably, glycosyl is fructosyl.

The term "thioureidyl residue" as used herein refers to a substituent bonded to a nitrogen atom to form a —N—C(S)—NR'₂ group, wherein each R' is independently selected from a hydrogen atom or R" as defined above. Preferably R' is a hydrogen atom or an optionally substituted aliphatic and more preferably one R' is a hydrogen atom and the other R' is an optionally substituted aliphatic.

The term "ester" refers to a group —C(O)O—R, wherein R is, for example, optionally substituted aliphatic, carbocycle or heterocycle.

The term "alkoxy" as used herein refers to a group of the form —O—R, wherein R is alkyl, preferably lower alkyl.

The term "aminoacyl residue" refers to a moeity comprising an optionally substituted aminoacyl group, wherein an amino acyl group as used herein refers to an acyl group substituted with an amine, monoalkylamine or dialkylamine at the α or β position relative to the carbonyl. Aminoacyl may be substituted by one or more substituents as described above. In some embodiments, aminoacyl may be substituted by one or more substituents independently selected from the group consisting of optionally substituted aliphatic, alkoxy, aralkyl, heteroaralkyl, carbocyclo, heterocyclo, alkylcarbonyloxy, alkoxycarbonyl or alkylcarbonyl. Preferred substituents include optionally substituted lower alkyl, alkylamino (monoalkylamino or dialkylamino), aralkyl, heteroaralkyl, carbocyclo and heterocyclo.

The terms "aralkyl" and "heteroaralkyl" as used herein refers to an alkyl group as defined above substituted with an aryl or heteroaryl group as defined above. The alkyl component of an "aralkyl" or "heteroaralkyl" group may be substituted with any one or more of the substituents listed above for an aliphatic group and the aryl or heteroaryl component of an "aralkyl" or "heteroaralkyl" group may be substituted with any one or more of the substituents listed above for aryl, heteroaryl, carbocycle or heterocycle groups. Preferably, aralkyl is benzyl.

In compounds of the invention, one or more asymmetric carbon atoms may be present. For such compounds, the invention is understood to include all isomeric forms (e.g. enantiomers and diastereoisomers) of the compounds as well as mixtures thereof, for example racemic mixtures.

A compound of the invention, including salts, hydrates and complexes thereof, may in some embodiments be provided in a water soluble form. A compound can be considered to be water soluble, for example, if it will dissolve in water at room temperature (20° C.), optionally with heating, agitation or sonication. In some embodiments, a compound of the invention (e.g. in a salt form) may be considered water soluble if it is soluble in water at room temperature at a concentration of at least 10 mg/ml, preferably at least 20 mg/ml. As described herein, a compound of the invention may also be provided in the form of a complex, with a complexing agent. In the context of the invention, a complex may be considered to be water soluble if it forms a transparent colloidal suspension in water, for example under the conditions mentioned above.

The term "complexing compound" as used herein refers to a compound with which a compound of the invention can form a non-covalent complex. Complexing compounds can include, for example, calcium salts, succinic acid, sodium deoxycholate or sterols.

DETAILED DESCRIPTION OF INVENTION

In a first aspect, the invention provides sterically hindered derivatives of Nystatin $A_1$ according to the Formula 1a:

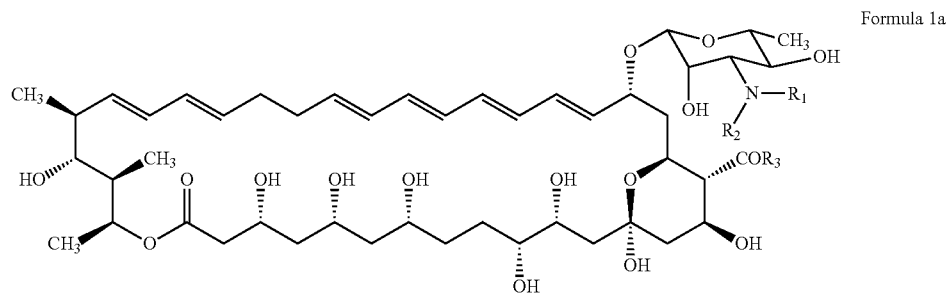

Formula 1a or a salt, hydrate or complex thereof;
wherein $R_1$ is independently chosen from a hydrogen atom, optionally substituted alkyl (preferably a non-branched alkyl or a substituted alkyl), an optionally substituted succinimidyl derivative, a glycosyl residue, an optionally substituted aminoacyl residue, or an optionally substituted thioureidyl residue;
$R_2$ is a hydrogen atom or a substituent such as defined for $R_1$;
$R_3$ is a hydroxyl group, alkoxyl group or an alkylamino or aminoalkyl derivative.

In a preferred embodiment of a compound of Formula 1a as defined above, when $R_3$ is hydroxyl, $R_1$ and $R_2$ are not both a hydrogen atom.

In some embodiments a compound of Formula 1a as defined above may be a compound according to Formula 1b

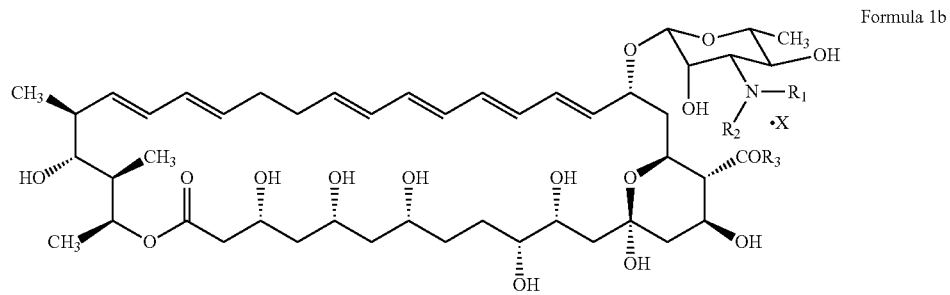

Formula 1b or a salt or complex thereof;
wherein $R_1$, $R_2$ and $R_3$ are as defined in claim 1;
X is absent or present and, when present, X is one or more molecules of base or acid, or complexing compound.

In some embodiments a compound of the invention is a compound according to Formula 1b

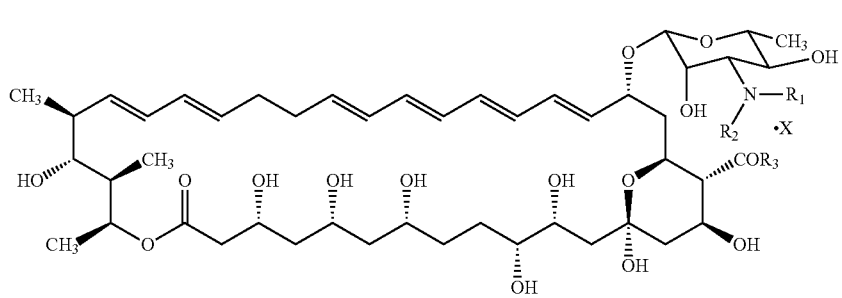

Formula 1b wherein R₁ is chosen from the group comprising: a hydrogen atom, a non-branched alkyl, an optionally substituted or spatially expanded alkyl, including a succinimidyl derivative, an alkyl derivative containing carbo- or heterocyclic moieties, a glycosyl residue, an optionally substituted or spatially expanded aminoacyl residue or thioureidyl residue optionally substituted with a bulky aliphatic or cyclic substituent containing at least one basic nitrogen atom;

R₂ is hydrogen atom or substituents such as defined for R₁,

R₃ is hydroxyl group, or alkoxyl group or an aminoalkyl derivative;

and their water-soluble salt or complexes, where X is one or more molecules of base or acid, or complexing compound.

In further embodiments, the invention provides a compound wherein one or both of R₁ and R₂ is alkyl substituted with an optionally substituted alkylamino or an optionally substituted carbo- or heterocyclic moiety. In some embodiments one or both of R₁ and R₂ is, independently, dialkylamino or optionally substituted N-linked heterocycle (preferably heterocycloalkyl). In some embodiments, N-linked heterocycle is unsubstituted or substituted with alkyl.

In further embodiments, the invention provides a compound wherein one or both (preferably one) of R₁ or R₂ is a succinimidyl derivative of structure

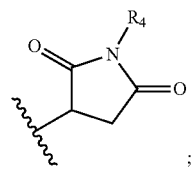

and wherein R₄ is X—Y, wherein X is an optionally substituted alkyl or a single bond; and Y is an optionally substituted carbo- or heterocyclic moiety or NR*₂, NH₂, NHR*, where R* is an optionally substituted aliphatic, or an optionally substituted carbo- or heterocyclic moiety, or two R* form, together with the nitrogen atom to which they are bound, an optionally substituted heterocycle. Preferably, Y is an optionally substituted carbo- or heterocyclic moiety or a dialkylamino. X may be branched or non-branched alkyl, e.g. lower alkyl. In some embodiments, Y is unsubstituted or substituted with one or more of alkyl or halo.

In further embodiments, the invention provides a compound wherein one or both (preferably one) of R₁ or R₂ is a thioureidyl or structure

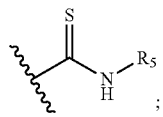

and wherein R₅ is in the form W—Z, wherein W is an optionally substituted alkyl; and Z is an optionally substituted nitrogen-containing heterocycle, preferably nitrogen-linked, or NR*₂, NH₂, NHR*, where R* is an optionally substituted aliphatic, or an optionally substituted carbo- or heterocyclic moiety, or two R* form, together with the nitrogen atom to which they are bound, an optionally substituted heterocycle. W may be branched or non-branched alkyl, e.g. lower alkyl. In some embodiments, Z is unsubstituted or substituted with one or more of alkyl or halo.

In further embodiments, the invention provides a compound wherein one or both (preferably one) of R₁ or R₂ is a aminoacyl of structure

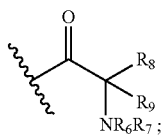

and wherein;

R₆ and R₇ are independently chosen from a hydrogen atom or an optionally substituted alkyl, or R₆ and R₇ can be taken, together with the atom to which they are joined, to form an optionally substituted nitrogen-containing cyclic moiety; R₈ and R₉ are, independently, hydrogen or —U—V, wherein U is an optionally substituted alkyl linker (preferably lower alkyl) or a single bond and V is a hydrogen atom, or an optionally substituted aliphatic, carbocyclic (preferably aryl), heterocyclic (preferably heteroaryl or heterocycloalkyl), alkoxy, or ester moiety. In some embodiments, one of R₈ and R₉ is hydrogen.

In further embodiments, the invention provides a compound wherein one or both (preferably one) of R₁ or R₂ is a aminoacyl of structure

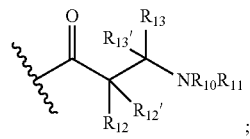

and wherein;

$R_{10}$ and $R_{11}$ independently chosen from a hydrogen atom or an optionally substituted alkyl or $R_{10}$ and $R_{11}$ can be taken, together with the atom to which they are joined, to form an optionally substituted nitrogen-containing cyclic moiety;

$R_{12}$, and $R_{13}$ are, independently, hydrogen or —U—V, wherein U is an optionally substituted alkyl linker (preferably lower alkyl) or a single bond and V is a hydrogen atom, or an optionally substituted aliphatic, carbocyclic (preferably aryl), heterocyclic (preferably heteroaryl or heterocycloalkyl), alkoxy, or ester moiety; and $R_{12'}$ and $R_{13'}$ are, independently, hydrogen or alkyl (preferably lower alkyl), preferably both $R_{12'}$ and $R_{13'}$ are hydrogen.

In further embodiments, a compound as described herein may be provided in the form of a salt with an inorganic or organic base, preferably as salt with N-methylglucamine.

In further embodiments, a compound as described herein may be provided in the form of a complex with an inorganic or organic complexing compound, preferably as a complex with a calcium salt, succinic acid, sodium deoxycholate or a sterol.

In further embodiments, a compound as described herein may be provided in form of salt with an inorganic or organic acid, preferably with aspartic acid.

Any of the salts or complexes as described above may be water soluble.

In another embodiment, the invention provides a compound of Formula 1:

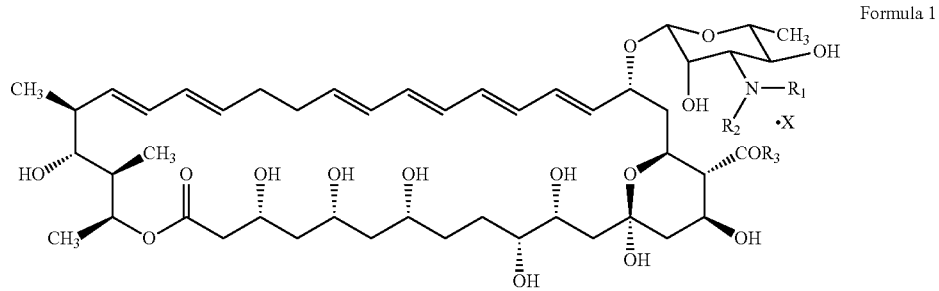

Formula 1

In further embodiments, the invention provides a compound wherein one or both (preferably one) of $R_1$ or $R_2$ is a glycosyl residue, preferably a fructosyl residue.

In some embodiments, the invention provides a compound wherein one of $R_1$ and $R_2$ is a hydrogen atom or an unsubstituted alkyl (preferably non-branched) or a substituted alkyl; and the other of $R_1$ and $R_2$ is an unsubstituted non-branched alkyl, a substituted alkyl, a succinimidyl derivative, a glycosyl residue, an optionally substituted aminoacyl residue, or an optionally substituted thioureidyl residue. In some preferred embodiments, one of $R_1$ and $R_2$ is a hydrogen atom or a non-branched alkyl or alkyl substituted with alkylamino or an optionally substituted carbo- or heterocyclic moiety (preferably a N-linked heterocycloalkyl, optionally substituted with alkyl); and the other of $R_1$ and $R_2$ is an unsubstituted non-branched alkyl, a substituted alkyl, a succinimidyl derivative, a glycosyl residue, an optionally substituted aminoacyl residue, or an optionally substituted thioureidyl residue as described in respect of any of the classes or subclasses of compounds above.

In preferred embodiments, the invention provides a compound wherein $R_3$ is hydroxyl, methoxy, or —$NR_{14}$—($C_1$-$C_6$alkyl)-$NR_{15}R_{16}$, wherein $R_{14}$ is a hydrogen atom or methyl, $R_{15}$ and $R_{16}$ are independently chosen from optionally substituted aliphatic, preferably lower alkyl.

In preferred embodiments, the invention provides a compound wherein the hemotoxicity expressed by $EH_{50}$ value is greater than 200 μg/ml, preferably greater than 300 μg/ml.

In some embodiments, the invention provides a compound of any of the subclasses described above wherein $R_1$ is any of the groups as listed for $R_1$ in Table 1.

In some embodiments, the invention provides a compound of any of the subclasses described above wherein $R_2$ is any of the groups as listed for $R_2$ in Table 1.

In some embodiments, the invention provides a compound of any of the subclasses described above wherein $R_3$ is any of the groups as listed for $R_3$ in Table 1.

where $R_1$ is hydrogen atom or alkyl substituent simple or spatially enlarged, advantageously as residue of succinimidyl derivative or alkyl containing carbo- or heterocyclic ring moieties or glycosyl residue or spatially branched aminoacyl residue or thioureidyl residue containing basic nitrogen atom and spacially branched aliphatic or cyclic substituents;

$R_2$ is hydrogen atom or substituents such as designated for $R_1$, while $R_3$ is hydroxyl group, alkoxyl, or aminoalkyl, and their salts and complexes being water soluble forms, where X is one or more molecules of base or acid, or complexing compound.

According to the invention in an advantageous variant, the compounds of structure presented by Formula 1, 1a or 1b characterized by the presence of bulky moieties which could induce steric hindrance effect, attached to amino group of mycosamine residue have been obtained in several versions, all of which are exemplary embodiments of the invention:

N-succinimidyl derivatives from N1 to N11, exemplary including: N—(N'-benzylsuccinimidyl)nystatin $A_1$ (N1), N—(N'-4-bromophenylsuccinimidyl)nystatin $A_1$ (N2), N—(N'-2,4,6-trimethylphenylsuccinimidyl)nystatin $A_1$ (N3), N—(N'-2,6-dimethyl-phenylsuccinimidyl)nystatin $A_1$ (N4), N—(N'-cyclohexylsuccinimidyl)nystatin $A_1$ (N5); N—(N'-amino)succinimidyl derivatives exemplary including: N—[N'-3-(N'',N''-dimethylamino)propylsuccinimidyl]nystatin $A_1$ (N6), N—[N'-2-(N'',N''-dimethylamino) ethylsuccinimidyl]nystatin $A_1$ (N7), N—[N'-2-(piperidin-1-yl) ethylsuccinimidyl]nystatin $A_1$ (N8), N—[N'-2-(4-methylpiperazin-1-yl)ethylsuccinimidyl]nystatin $A_1$ (N9), N—[N'-3-(N'',N''-dimethylamino)-2,2-dimethylpropylsuccinimidyl]nystatin $A_1$ (N10), N—[N'-2-(pyrrolidin-1-yl)ethylsuccinimidyl]nystatin $A_1$ (N11);

Thioureidyl derivatives from N12 to N20, exemplary including: N-{3-[2-(piperidin-1-yl)ethyl]thioureidyl}nystatin $A_1$ (N12), N-{3-[2-(morpholin-1-yl)ethyl]thioureidyl}nystatin $A_1$ (N13), N-{3-[2-(N,N-diethylamino)ethyl]thioureidyl}nystatin A$_1$ (N14), N-{3-[2-(4-methylpiperazin-1-yl)ethyl]thioureidyl}nystatin A$_1$ (N15), N-{3-[2-(pyrrolidin-1-yl)ethyl]thioureidyl}nystatin A$_1$ (N16), N-{3-[3-(N,N-dimethylamino)propyl]thioureidyl}nystatin A$_1$ (N17), N-{3-[2-(N,N-dimethylamino)ethyl]thioureidyl}nystatin A$_1$ (N18), N-{3-[3-(N,N-dimethylamino)-2,2-dimethylpropyl]thioureidyl}nystatin A$_1$ (N19), N-{3-[3-(imidazo-1-yl)propyl]thioureidyl}nystatin A$_1$ (N20);

N-benzyl derivatives exemplary including: N-benzylnystatin A$_1$ (N21);

N-alkyl derivatives from N22 to N26, exemplary including: N,N-di-n-propylnystatin A$_1$ (N22), N,N-dimethylnystatin A$_1$ (N23), N,N-diethylnystatin A$_1$ (N24), N,N-di(3-(piperidin-1-yl)propyl]nystatin A$_1$ (N25), N,N-di[3-(4-ethylpiperazin-1-yl)propyl]nystatin A$_1$ (N26);

N-alkyl derivatives of N-fructosylnystatin A$_1$ from N27 to N32, exemplary including: N-fructosyl-N-n-propylnystatin A$_1$ (N27), N-fructosyl-N-methylnystatin A$_1$ (N28), N-fructosyl-N-ethylnystatin A$_1$ (N29), N-fructosyl-N-[3-(N',N'-dimethylamin) propyl]nystatin A$_1$ (N30), N-fructosyl-N-[3-(piperidin-1'-yl)propyl]nystatin A$_1$ (N31), N-fructosyl-N-[3-(4-ethylpiperazin-1-yl)propyl)]nystatin A$_1$ (N32);

N-aminoacyl and N—(N'-alkylamino)acyl Nystatin A$_1$ derivatives from N33 to N43, exemplary including: N-D-phenylglycylnystatin A$_1$ (N33), N-L-phenylalanylnystatin A$_1$ (N34), N-L-(O-tert-butyl)glutamylnystatin A$_1$ (N35), N-L-(O-tert-butyl)serylnystatin A$_1$ (N36), N-D-(O-tert-butyl)glutamylnystatin A$_1$ (N37), N-D-(O-tert-butyl)serylnystatin A$_1$ (N38), N-D-β-naphtylalanylnystatin A$_1$ (N39), N-L-(4-nitrophenyl)alanylnystatin A$_1$ (N40), N-D-(O-tert-butyl) asparagylnystatin A$_1$ (N41), N-D-β-(pyridin-3-yl) alanylnystatin A$_1$ (N42), N-[2-(N-methylamino)-2-methylpropan]nystatin A$_1$ (N43); N—(N,N-dialkylamino) alkylacyl derivatives of Nystatin A$_1$ from N44 to N50, exemplary including: N-[3-(piperidin-1-yl)propionyl]nystatin A$_1$ (N44), N-[L-(N,N-dimethyl)phenylalanyl]nystatin A$_1$ (N45); N—[L-(N,N-diethyl)phenylalanyl]nystatin A$_1$ (N46), N—[(N,N-di-n-propyl)glycyl]nystatin A$_1$ (N47), N-[3-(N,N-di-n-propylamino)propionyl]nystatin A$_1$ (N48), N-[3-(N,N-diethylamino) propionyl]nystatin A$_1$ (N49), N-[3-(N,N-dimethylamino)propionyl]nystatin A$_1$ (N50);

Methyl esters of N-substituted derivatives of Nystatin A$_1$ from NM to NM exemplary including: N-{3-[3-(N,N-dimethylamino)-2,2-dimethylpropyl]thioureidyl}nystatin A$_1$ methyl ester (N51), N,N-di-n-propylnystatin methyl ester A$_1$ (N52), N-fructosyl-N-n-propylnystatin A$_1$ methyl ester (N53), N-D-phenylglycylnystatin A$_1$ methyl ester (N54);

Amides of N-substituted derivatives of Nystatin A$_1$ from N55 to N58, exemplary including: N-{3-[3-(N,N-dimethylamino)-2,2-dimethylpropyl]tioureidyl}nystatin A$_1$ 3-(N,N-dimethyl-amino)propylamide (N55), N,N-di-n-propylnystatin A$_1$ 3-(N,N-dimethylamino)propylamide (N56), N-fructosyl-N-n-propylnystatin A$_1$ 3-(N,N-dimethylamino)propylamide (N57), N-D-phenylglycylnystatin A$_1$ 3-(N,N-dimethyl-amino)propylamide (N58);

According to the invention, water soluble salts of amphoteric derivatives of Nystatin A$_1$ with bases, exemplary including N-methyl-D-glucamine salt of N-fructosyl-N-n-propylnystatin A$_1$ were obtained (N59);

According to the invention, water soluble complexes of amphoteric derivatives of Nystatin A$_1$, can be obtained according to know procedure for native Nystatin A$_1$;

Water soluble salts of basic Nystatin A$_1$ derivatives with acids, exemplary L-aspartate of N-fructosyl-N-n-propylnystatin A$_1$ methyl ester, were obtained (N60).

In some embodiments, a compound as described herein has hemotoxicity expressed by $EH_{50}$ value of greater than 200 µg/ml, preferably greater than 300 µg/ml.

Structures of Nystatin A$_1$ derivatives, according to the invention, are presented below in Table 1. Nystatin structure is provided for reference purposes.

TABLE 1

Structures of Nystatin A$_1$ derivatives.

| Lp | Symbol | R$_1$ | R$_2$ | R$_3$ |
|---|---|---|---|---|
| | Nystatin | —H | —H | —OH |
| | | | N-succinimidyl derivatives | |
| 1 | N1 | —H | [structure] | —OH |
| 2 | N2 | —H | [structure] | —OH |
| 3 | N3 | —H | [structure] | —OH |

TABLE 1-continued
Structures of Nystatin $A_1$ derivatives.
| Lp | Symbol | $R_1$ | $R_2$ | $R_3$ |
|----|--------|-------|-------|-------|
| 4 | N4 | —H | 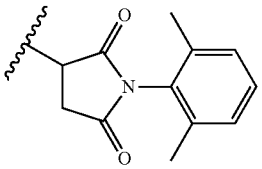 [SMILES: *C1CC(=O)N(c2c(C)cccc2C)C1=O] | —OH |
| 5 | N5 | —H | 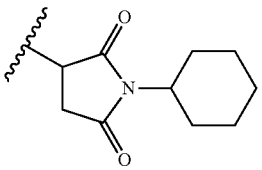 [SMILES: *C1CC(=O)N(C2CCCCC2)C1=O] | —OH |
| 6 | N6 | —H | 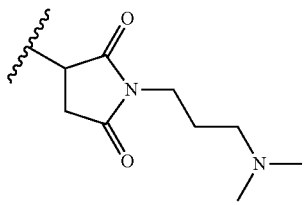 [SMILES: *C1CC(=O)N(CCCN(C)C)C1=O] | —OH |
| 7 | N7 | —H | 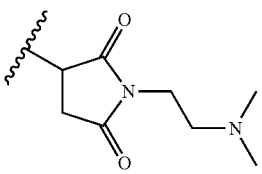 [SMILES: *C1CC(=O)N(CCN(C)C)C1=O] | —OH |
| 8 | N8 | —H | 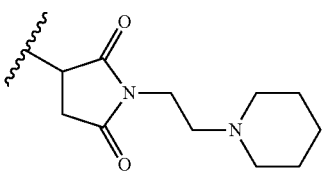 [SMILES: *C1CC(=O)N(CCN2CCCCC2)C1=O] | —OH |
| 9 | N9 | —H | 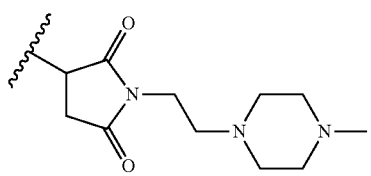 [SMILES: *C1CC(=O)N(CCN2CCN(C)CC2)C1=O] | —OH |
| 10 | N10 | —H | 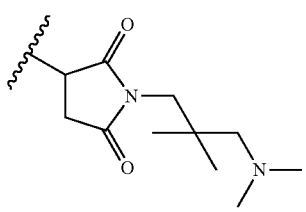 [SMILES: *C1CC(=O)N(CC(C)(C)CN(C)C)C1=O] | —OH |
| 11 | N11 | —H | 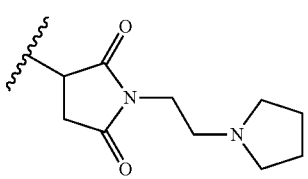 [SMILES: *C1CC(=O)N(CCN2CCCC2)C1=O] | —OH |

TABLE 1-continued
Structures of Nystatin A₁ derivatives.
| Lp | Symbol | R₁ | R₂ | R₃ |
|----|--------|-----|-----|-----|
| Thioureidyl derivatives | | | | |
| 12 | N12 | —H | 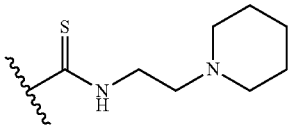 [SMILES: *C(=S)NCCN1CCCCC1] | —OH |
| 13 | N13 | —H | 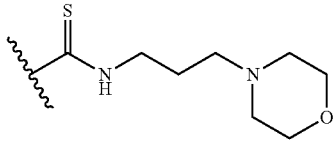 [SMILES: *C(=S)NCCCN1CCOCC1] | —OH |
| 14 | N14 | —H | 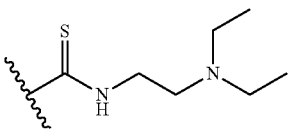 [SMILES: *C(=S)NCCN(CC)CC] | —OH |
| 15 | N15 | —H | 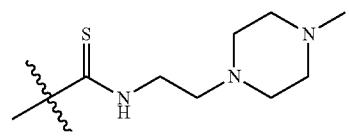 [SMILES: *C(=S)NCCN1CCN(C)CC1] | —OH |
| 16 | N16 | —H | 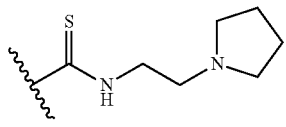 [SMILES: *C(=S)NCCN1CCCC1] | —OH |
| 17 | N17 | —H | 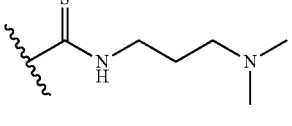 | —OH |
| 18 | N18 | —H | 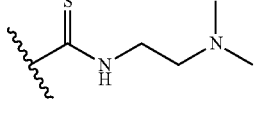 | —OH |
| 19 | N19 | —H | 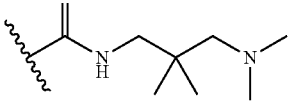 | —OH |
| 20 | N20 | —H | 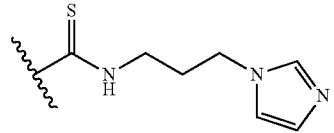 [SMILES: *C(=S)NCCCn1ccnc1] | —OH |
| N-alkyl derivatives | | | | |
| 21 | N21 | —H | 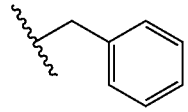 [SMILES: *Cc1ccccc1] | —OH |
| 22 | N22 | —CH₂CH₂CH₃ | —CH₂CH₂CH₃ | —OH |
| 23 | N23 | —CH₃ | —CH₃ | —OH |
| 24 | N24 | —CH₂CH₃ | —CH₂CH₃ | —OH |

TABLE 1-continued

Structures of Nystatin A₁ derivatives.

| Lp | Symbol | R₁ | R₂ | R₃ |
|----|--------|----|----|----|
| 25 | N25 | (4-piperidin-1-yl-butyl) | (4-piperidin-1-yl-butyl) | —OH |
| 26 | N26 | (4-(4-ethylpiperazin-1-yl)butyl) | (4-(4-ethylpiperazin-1-yl)butyl) | —OH |
| 27 | N27 | mycosamine sugar | —CH₂CH₂CH₃ | —OH |
| 28 | N28 | mycosamine sugar | —CH₃ | —OH |
| 29 | N29 | mycosamine sugar | —CH₂CH₃ | —OH |
| 30 | N30 | mycosamine sugar | (3-dimethylaminopropyl) | —OH |
| 31 | N31 | mycosamine sugar | (4-piperidin-1-yl-butyl) | —OH |
| 32 | N32 | mycosamine sugar | (4-(4-ethylpiperazin-1-yl)butyl) | —OH |

TABLE 1-continued

Structures of Nystatin A₁ derivatives.

| Lp | Symbol | R₁ | R₂ | R₃ |
|----|--------|-----|-----|-----|

N-aminoacyl derivatives

| 33 | N33 | —H | phenylglycinyl (C(=O)-CH(NH₂)-C₆H₅) | —OH |
| 34 | N34 | —H | phenylalaninyl (C(=O)-CH(NH₂)-CH₂-C₆H₅) | —OH |
| 35 | N35 | —H | glutamic acid γ-tert-butyl ester acyl | —OH |
| 36 | N36 | —H | serine O-tert-butyl ether acyl | —OH |
| 37 | N37 | —H | glutamic acid γ-tert-butyl ester acyl | —OH |
| 38 | N38 | —H | serine O-tert-butyl ether acyl | —OH |
| 39 | N39 | —H | 1-naphthylalaninyl | —OH |
| 40 | N40 | —H | 4-nitrophenylalaninyl | —OH |
| 41 | N41 | —H | aspartic acid β-tert-butyl ester acyl | —OH |

TABLE 1-continued

Structures of Nystatin A₁ derivatives.

| Lp | Symbol | R₁ | R₂ | R₃ |
|---|---|---|---|---|
| 42 | N42 | —H | 2-amino-3-(pyridin-3-yl)propanoyl | —OH |
| 43 | N43 | —H | 2-methyl-2-(methylamino)propanoyl | —OH |
| 44 | N44 | —H | 4-(piperidin-1-yl)-2-methylbutanoyl | —OH |
| 45 | N45 | —H | 2-(dimethylamino)-3-phenylpropanoyl | —OH |
| 46 | N46 | —H | 2-(diethylamino)-3-phenylpropanoyl | —OH |
| 47 | N47 | —H | 3-(dipropylamino)-2-oxopropyl | —OH |
| 48 | N48 | —H | 4-(dipropylamino)-2-methylbutanoyl | —OH |
| 49 | N49 | —H | 4-(diethylamino)butanoyl | —OH |
| 50 | N50 | —H | 4-(dimethylamino)-2-methylbutanoyl | —OH |

TABLE 1-continued

Structures of Nystatin A₁ derivatives.

| Lp | Symbol | R₁ | R₂ | R₃ |
|----|--------|----|----|----|
| di-modified ester derivatives | | | | |
| 51 | N51 | —H | 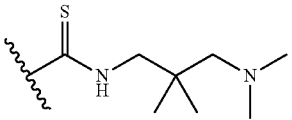 | —OCH₃ |
| 52 | N52 | —CH₂CH₂CH₃ | —CH₂CH₂CH₃ | —OCH₃ |
| 53 | N53 | 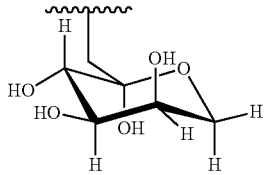 | —CH₂CH₂CH₃ | —OCH₃ |
| 54 | N54 | —H | 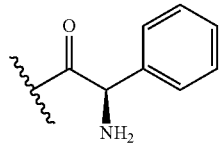 [SMILES: *C(=O)[C@H](N)c1ccccc1] | —OCH₃ |
| di-modified amide derivatives | | | | |
| 55 | N55 | —H | 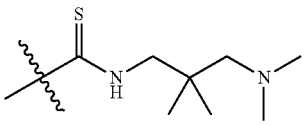 [SMILES: *C(=S)NCC(C)(C)CN(C)C] | —NHCH₂CH₂CH₂N(CH₃)₂ |
| 56 | N56 | —CH₂CH₂CH₃ | —CH₂CH₂CH₃ | —NHCH₂CH₂CH₂N(CH₃)₂ |
| 57 | N57 | 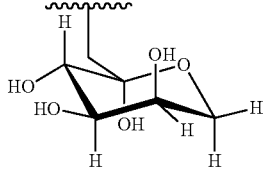 | —CH₂CH₂CH₃ | —NHCH₂CH₂CH₂N(CH₃)₂ |
| 58 | N58 | —H | 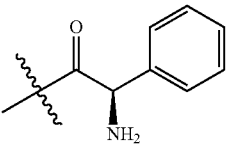 | —NHCH₂CH₂CH₂N(CH₃)₂ |

The idea of the invention includes also application of the compounds being sterically hindered derivatives of antifungal antibiotic Nystatin A₁ of Formula 1, 1a or 1b, where R₁ is a hydrogen atom or simple non-branched or bulky alkyl, advantageously as residue of succinimide derivative or alkyl containing cyclic moieties carbo- or heterocyclic, glycosyl residue or bulky aminoacyl residue or thioureidyl residue containing basic nitrogen atom and bulky aliphatic or cyclic substituents, R₂ is hydrogen atom or substituents such as are defined for R₁, while R₃ is hydroxyl group or alkoxyl or aminoalkyl group also their salts and complexes being water soluble forms, where X is one or more molecules of base or acid or complexing compound, for the control of fungal microorganisms, preferably of multidrug resistance once directly or as active components for various formulations of antifungal drugs.

In a second aspect, the invention provides a pharmaceutical composition comprising a compound according to the invention as defined herein. As referenced throughout, a compound according to the invention includes salts, hydrates and complexes thereof.

In a third aspect, the invention provides a compound as defined herein, for use in the treatment of fungal infection. The compound may also be for use in the treatment of diseases caused by fungal infection. Treatment may be in humans or in veterinary medicine.

In a fourth aspect, the invention provides use of a compound in the manufacture of a medicament for the treatment of fungal infection, diseases caused by fungal infection, including treatment in humans or in veterinary medicine.

In a fifth aspect, the invention provides a method of treating diseases caused by fungal infection in a patient comprising administering the patient a therapeutically effective amount of a compound of the invention, wherein the patient is a human or animal.

In a sixth aspect, the invention provides the use of a compound of the invention for treating a fungal infection in a plant.

In a seventh aspect, the invention provides a plant protection product comprising a compound of the invention.

In some embodiments, treatment as referred to herein relates to treatment of fungal infections caused by a strain of the genus *Candida*. This may be a strain of the genus *Candida* having multidrug resistance (MDR).

Compounds of the invention, when used for preventing or treating a disease, may be administered in an "effective amount". By an "effective amount" it is meant a "therapeutically effective amount", namely an amount of compound sufficient, upon single dose or multiple dose administration, to cause a detectable decrease in disease severity, to prevent advancement of a disease or alleviate disease symptoms beyond that expected in the absence of treatment.

Compounds of the invention are useful for reducing the severity of symptoms of any of the above disorders to be treated. Compounds of the invention are also useful for administration to patients susceptible to, at risk of or suffering from any of the above disorders. Compounds useful for prevention of the above disorders are not required to absolutely prevent occurrence of the disorder in all cases, but may prevent or delay onset of the disorder when administered to a patient susceptible to or at risk of the disorder.

The compounds of the invention may be provided as the free compound or as a suitable salt or hydrate thereof. Salts should be those that are pharmaceutically acceptable and salts and hydrates can be prepared by conventional methods, such as contacting a compound of the invention with an acid or base whose counterpart ion does not interfere with the intended use of the compound. Examples of pharmaceutically acceptable salts include hydrohalogenates, inorganic acid salts, organic carboxylic acid salts, organic sulfonic acid salts, amino acid salt, quaternary ammonium salts, alkaline metal salts, alkaline earth metal salts and the like.

The compounds of the invention can be provided as a pharmaceutical composition. The pharmaceutical composition may additionally comprise a pharmaceutically acceptable excipient for example a pharmaceutically acceptable carrier and/or a pharmaceutically acceptable diluent. Suitable carriers and/or diluents are well known in the art and include pharmaceutical grade starch, mannitol, lactose, magnesium stearate, sodium saccharin, talcum, cellulose, glucose, sucrose (or other sugar), magnesium carbonate, gelatin oil, alcohol, detergents, emulsifiers or water (preferably sterile).

A pharmaceutical composition may be provided in unit dosage form, will generally be provided in a sealed container and may be provided as part of a kit. Such a kit would normally (although not necessarily) include instructions for use. It may include a plurality of said unit dosage forms.

A pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with a carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts, buffers, coating agents or antioxidants. They may also contain an adjuvant and/or therapeutically active agents in addition to the substance of the present invention.

Dosages of the substance of the present invention can vary between wide limits, depending upon a variety of factors including the disease or disorder to be treated, the age, weight and condition of the individual to be treated, the route of administration etc. and a physician will ultimately determine appropriate dosages to be used.

Below are described methods for obtaining compounds which are bulky, spatially hindered amphoteric or basic N-alkyl or N-aminoacyl derivatives of antifungal antibiotic of polyene macrolides group, Nystatin $A_1$, of general Formula 1, 1a or 1b, where $R_1$ is hydrogen atom or simple or bulky alkyl substituent, the last one preferably as a residue of succinimide derivative, or branched alkyl or containing cyclic carbo- or heterocyclic moieties or glycosyl residue, or bulky, spatially extended aminoacyl residue or thioureidyl residue containing basic nitrogen atom and bulky aliphatic or cyclic substituents; $R_2$ is hydrogen atom or substituents such as are defined for $R_1$, while $R_3$ is hydroxyl group or alkoxyl or aminoalkyl group, also their salts and complexes being their water soluble forms, where X is one or more basic molecules, advantageously N-methyl-D-glucamine or acid molecule, preferably aspartic acid, or complexing agent, preferably sodium deoxycholate.

To obtain N-succinimidyl derivatives, reaction of Michael's addition is performed as follows: solution of Nystatin $A_1$ in dimethyl formamide, in the presence of triethylamine, is reacted with suitable derivative of maleimide. The product is precipitated by ethyl ether, centrifuged, dried and purified by column chromatography (Silica Gel).

N-aminosuccinimidyl derivatives are obtained in similar manner as N-succinimidyl derivatives, but a two-fold excess of maleimide derivative is used.

N-thioureidyl derivatives are obtained in the reaction of Nystatin $A_1$ in dimethyl formamide solution and in the presence of triethylamine with a proper derivative of isothiocyanate, then the reaction product is purified by column chromatography (Silica Gel).

N-benzyl derivatives are obtained in the reaction of reductive alkylation of Nystatin $A_1$, in solution of dimethyl formamide and methanol, with benzaldehyde or its derivatives, using sodium cyanoborohydride as a reducing agent and a catalytic amount of acetic acid. The reaction mixture is neutralized with solution of methylamine in tetrahydrofuran, then the final product is precipitated by ethyl ether and purified by column chromatography (Silica Gel).

N-alkyl derivatives of Nystatin $A_1$ are obtained in the reaction of reductive alkylation of Nystatin $A_1$, in solution of dimethyl formamide, with aliphatic aldehyde using sodium cyanoborohydride as a reducing agent and a catalytic amount of acetic acid. The reaction mixture is neutralized with solution of methylamine in tetrahydrofuran, the product is precipitated by ethyl ether, and then purified by column chromatography (Silica Gel).

The synthesis of N-alkyl derivatives of N-fructosylnystatin $A_1$ is based on method of reductive alkylation of N-fructosylnystatin $A_1$, in solution of dimethyl formamide, with suitable aliphatic aldehyde and sodium cyanoborohydride as a reducing agent and a catalytic amount of acetic acid. The neutralization of reaction mixture is performed by adding of methylamine in tetrahydrofuran, then reaction product is precipitated by ethyl ether and purified by column chromatography (Silica Gel).

N-aminoacyl and N—(N' alkylamino)acyl derivatives of Nystatin $A_1$ are obtained in the reaction of N-acylation of antibiotic by appropriate N-protected aminoacid. First, the reaction of N-(9-fluorenylmetoxycarbonyl)-aminoacid with N-hydroxysuccinimide in the presence of N,N'-dicyclohexylcarbodiimide is performed in solution of dimethyl formamide. Precipitated solid of N,N'-dicyclohexylurea is removed, then to the reaction mixture Nystatin $A_1$ and triethyamine are added, monitoring progress of the reaction by thin layer chromatography. The final product is precipitated with ethyl ether and next purified by column chromatography (Silica Gel);

Synthesis of N—(N',N'-dialkyloamino)aminoacyl derivatives of Nystatin $A_1$ is performed by activation of an amino acid by N-hydroxysuccinimide and N,N'-dicyclohexylcarbodiimide in dimethyl formamide. Precipitated solid of N,N'-dicyclohexylurea is removed and Nystatin $A_1$ is added to the reaction mixture. Crude product of the reaction is precipitated by an excess of ethyl ether and purified by column chromatography (Silica Gel);

Synthesis of methyl esters of N-substituted Nystatin $A_1$ derivatives is performed in the reaction of antibiotic, in dimethyl formamide solution, with diazomethane which is added to the reaction mixture in ethyl ether solution. Then, an excess of diazomethane is removed with acetic acid, the formed product is precipitated by an excess of ethyl ether and purified by column chromatography (Silica Gel);

Synthesis of amides of N-substituted Nystatin $A_1$ derivatives, on example of 3-(N,N-dimethylamino)propylamide of N-fructosyl-N-propylnystatin, is performed in the reaction of N-substituted antibiotic derivatives, in dimethyl formamide solution, with appropriate amine in the presence of diphenyl azidephosphate and triethylamine. The product of the reaction is precipitated by an excess of ethyl ether and purified by column chromatography (Silica Gel).

It will be appreciated that in the syntheses described above, the reagents used may be selected to prepare a compound of Formula 1, 1a or 1b, for example a compound having any of the substituents as illustrated for exemplary compounds of the invention in Table 1, in any combination.

Obtaining of salts of amphoteric Nystatin $A_1$ derivatives, advantageously with N-methyl-D-glucamine, consist in addition to aqueous suspension of Nystatin $A_1$ derivatives a small excess of N-methyl-D-glucamine diluted in water and precipitation of product by excess of acetone.

Water-soluble complex of amphoteric Nystatin $A_1$ derivatives with sodium deoxycholate can be obtained by the interacting the derivative with deoxycholate in phosphate buffer according to the standard procedure.

Water-soluble salts of basic Nystatin $A_1$ derivatives, advantageously with aspartic acid, are obtained by adding to aqueous suspension of antibiotic a slight molar excess of L-aspartic acid, then obtained salt is precipitated by excess of acetone.

The method for obtaining sterically hindered Nystatin $A_1$ derivatives, according to the invention, leads to the desired products. All obtained compounds have been characterized with respect to their chemical structure and biological properties. Identification data of the compounds include their spectroscopic data as $\lambda_{max}$ determination, extinction value of $E_{1\ cm}^{1\%}$, molecular weight determined by mass spectrometry MS-ESI, thin layer chromatographic characterization with indicated $R_F$ value. The biological properties of the compounds, according to the invention, were determined using the obligatory standards. There were determined activities of the compounds in vitro against a number of fungal strains, primarily of the genus *Candida*, and activity towards multidrug resistant fungal strains with overexpression of protein transporters of both ABC and MFS type. Also hemotoxicity of the compounds was determined by measurement of their hemolytic activity for human erythrocytes, as well as their cytotoxicity determined in tissue culture for several mammalian cell lines. The obtained results show that, depending on the kind of steric hindrance moieties introduced to Nystatin $A_1$ molecule, the compounds exhibit, reduced to different extent, in relation to native antibiotic, hemotoxic activity and are characterized by low cytotoxicity, good antifungal activity and are also active against multidrug resistant strains (MDR).

The advantage of the compounds, according to the invention, which are previously unknown sterically hindered derivatives of Nystatin $A_1$, is that they fulfill the essential requirements for antifungal chemotherapeutics. They are characterized by very low hemotoxicity, exhibit low toxicity towards mammalian cells, are active towards multidrug resistant fungal strains (MDR). Moreover, they form with acids and bases water-soluble salts and also soluble complexes with solubilizing complexing compounds. The advantage according to the invention is also simple and efficient method of their preparation.

According to the invention, can also be synthesized analogous derivatives of other antibiotics of tetraeno-diene polyene macrolides, like other components of Nystatin complex, namely Nystatin $A_2$ and $A_3$, components of Polyfungin complex including Polyfungin B and antibiotic Amphotericin A.

The subject of the invention is shown in the examples below, where are presented methods for the preparation and demonstrated properties of the compounds according to the invention, and of their water-soluble salts and complexes.

EXAMPLE 1

Synthesis of N-Succinimidyl Derivatives of Nystatin $A_1$ 200 mg (0.21 mmol) of Nystatin $A_1$ is dissolved in 4 ml of dimethyl formamide (DMF) in 100 ml round-bottomed flask equipped with a magnetic stirrer. The solution is cooled to 0° C. and 0.029 ml (0.21 mmol) of triethylamine (TEA) is slowly added. After 10 minutes 0.25 mmol of the appropriate maleimide is added and the reaction mixture is warmed to room temperature. The reaction progress is monitored by thin layer chromatography (TLC) on Silica Gel (60 F254, Merck) in chloroform:methanol:water (20:8:1 v/v) solvent system. After then, the reaction mixture is added dropwise to 150 ml of diethyl ether. The resulting, pale yellow precipitate, is filtered under reduced pressure on a Millipore funnel. The crude product is twice washed with diethyl ether (2×50 ml) and then dried in a vacuum desiccator. The residue is purified by column chromatography on normal phases, where the solid phase is Silica Gel and solvent system is chloroform:methanol:water (25:8:1 v/v). The fractions with pure product were collected and combined, then evaporated under reduced pressure at temperature not exceeding 35° C. Using in the reaction below indicated maleimides, the following derivatives of Nystatin $A_1$ are obtained:

a) In the reaction with N-benzylmaleimide is obtained 80 mg of N—(N'-benzylsuccinimidyl)nystatyn $A_1$ (N1)

TLC $R_f$=0.62; UV-vis: $\lambda_{max}$ (MeOH) 319; 304; 291 nm; $E_1{}_{cm}^{1\%}$ (MeOH, $\lambda$=304 nm)=500 (theoretically for $C_{58}H_{84}N_2O_{19}$ is 658); MS-ESI calculated for $C_{58}H_{84}N_2O_{19}$ [M+K]$^+$ 1150.6. found: 1150.1.

b) In the reaction with N-(4-bromophenyl)maleimide is obtained 92 mg of N—(N'-4-bromo phenylsuccinimidyl) nystatin $A_1$ (N2)

TLC $R_f$=0.55; UV-vis: $\lambda_{max}$ (MeOH) 319; 304; 291 nm; $E_1{}_{cm}^{1\%}$ (MeOH, $\lambda$=304 nm)=522 (theoretically for $C_{57}H_{81}BrN_2O_{19}$ is 621); MS-ESI calculated for $C_{57}H_{81}BrN_2O_{19}$ [M+H]$^+$ 1177.5; found: 1177.8.

c) In the reaction with N-(2,4,6-trimethylphenyl)maleimide is obtained 95 mg of N—(N'-2,4,6-trimethylphenylsuccinimidyl)nystatin $A_1$ (N3)

TLC $R_f$=0.77; UV-vis: $\lambda_{max}$ (MeOH) 319; 304; 291 nm; $E_1{}_{cm}^{1\%}$ (MeOH, $\lambda$=304 nm)=620 (theoretically for $C_{60}H_{88}N_2O_{19}$ is 641); MS-ESI calculated for $C_{60}H_{88}N_2O_{19}$ [M+H]$^+$ 1141.5; found: 1142.0.

d) In the reaction with N-(2,6-dimethylphenyl)maleimide is obtained 86 mg of N—(N'-2,6-dimethylphenylsuccinimidyl)nystatin $A_1$ (N4)

TLC $R_f$=0.58; UV-vis: $\lambda_{max}$ (MeOH) 319; 304; 291 nm; $E_1{}_{cm}^{1\%}$ (MeOH, $\lambda$=304 nm)=620 (theoretically for $C_{59}H_{86}N_2O_{19}$ is 649); MS-ESI calculated for $C_{59}H_{86}N_2O_{19}$ [M+H]$^+$ 1127.6; found: 1128.0.

e) In the reaction with N-cyclohexylmaleimide is obtained 60 mg of N—(N'-cyclohexyl succinimidyl)nystatin $A_1$ (N5)

TLC $R_f$=0.65; UV-vis: $\lambda_{max}$ (MeOH) 319; 304; 291 nm; $E_1{}_{cm}^{1\%}$ (MeOH, $\lambda$=304 nm)=630 (theoretically for $C_{57}H_{88}N_2O_{19}$ is 661); MS-ESI calculated for $C_{57}H_{88}N_2O_{19}$ [M+H]$^+$ 1105.6; found: 1106.0.

EXAMPLE 2

Synthesis of N—(N'-Alkyloamino)Succinimidyl Derivatives of Nystatin $A_1$ 200 mg (0.21 mmol) of Nystatin $A_1$ in 4 ml of dimethyl formamide (DMF) is dissolved in 100 ml round-bottomed flask equipped with a magnetic stirrer. The solution is cooled to 0° C. and 0.029 ml (0.21 mmol) of triethylamine (TEA) is slowly added. After 10 minutes 0.42 mmol of the appropriate basic maleimide is added and the reaction mixture is warmed to room temperature. The reaction progress is monitored by thin layer chromatography (TLC) on Silica Gel (60 F254, Merck) in chloroform:methanol:water (10:6:1 v/v) solvent system. After then, the reaction mixture is added dropwise to 150 ml of diethyl ether. The resulting, pale yellow precipitate, is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform:methanol (gradient from 20% to 80% of methanol). The fractions with pure product were collected and combined, then evaporated under reduced pressure at temperature not exceeding 35° C. Using in the reaction below indicated maleimide, the following derivatives of Nystatin $A_1$ are obtained:

a) In the reaction with N-3-(N',N'-dimethylamino)propylmaleimide is obtained 45 mg of N—[N'-3-(N'',N''-dimethylamino)propylsuccinimidyl]nystatin $A_1$ (N6)

TLC $R_f$=0.14; UV-vis: $\lambda_{max}$ (MeOH) 319; 304; 291 nm; $E_1{}_{cm}^{1\%}$ (MeOH, $\lambda$=304 nm)=600 (theoretically for $C_{56}H_{89}N_3O_{19}$ is 660); MS-ESI calculated for $C_{56}H_{89}N_3O_{19}$ [M+H]$^+$ 1108.3. found: 1108.6.

b) In the reaction with N-2-(N',N'-dimethylamino)ethylmaleimide is obtained 38 mg of N-[N'-2-(N''N''-dimethylamino)ethylsuccinimidyl]nystatin $A_1$ (N7)

TLC $R_f$=0.18; UV-vis: $\lambda_{max}$ (MeOH) 319; 304; 291 nm; $E_1{}_{cm}^{1\%}$ (MeOH, $\lambda$=304 nm)=540 (theoretically for $C_{55}H_{87}N_3O_{19}$ is 669); MS-ESI calculated for $C_{55}H_{87}N_3O_{19}$ [M+H]$^+$ 1094.3. found: 1094.6.

c) In the reaction with N-2-(piperidin-1-yl)ethylmaleimide is obtained 49 mg of N—(N'-2-(piperidin-1-yl)ethylsuccimidyl)nystatin $A_1$ (N8)

TLC $R_f$=0.34; UV-vis: $\lambda_{max}$ (MeOH) 319; 304; 291 nm; $E_1{}_{cm}^{1\%}$ (MeOH, $\lambda$=304 nm)=500 (theoretically for $C_{58}H_{91}N_3O_{19}$ is 645); MS-ESI calculated for $C_{58}H_{91}N_3O_{19}$ [M+H]$^+$ 1134.3. found: 1134.6.

d) In the reaction with N-2-(4-methylpiperazin-1-yl)ethylmaleimide is obtained 52 mg of N—[N'-2-(4-methylpiperazin-1-yl)ethylsuccinimidyl)nystatin $A_1$ (N9)

TLC $R_f$=0.11; UV-vis, (MeOH) 319; 304; 291 nm; $E_1{}_{cm}^{1\%}$ (MeOH, $\lambda$=304 nm)=570 (theoretically for $C_{58}H_{92}N_4O_{19}$ is 636); MS-ESI calculated $C_{58}H_{92}N_4O_{19}$ [M+H]$^+$ 1149.3. found: 1149.6.

e) In the reaction with N-3-(N',N'-dimethylamino)-2,2-dimethylpropylmaleimide is obtained 58 mg of N—[N'-3-(N'',N''-dimethyloamino)-2,2-dimethylpropylsuccinimidyl]nystatin $A_1$ (N10)

TLC $R_f$=0.25; UV-vis: $\lambda_{max}$ (MeOH) 319; 304; 291 nm; $E_1{}_{cm}^{1\%}$ (MeOH, $\lambda$=304 nm)=540 (theoretically for $C_{58}H_{93}N_3O_{19}$ is 644); MS-ESI calculated for $C_{58}H_{93}N_3O_{19}$ [M+H]$^+$: 1136.3. found: 1136.6.

f) In the reaction with N-2-(pyrrolidin-1-yl)ethylmaleimide is obtained 56 mg of N—[N'-2-(pyrrolidin-1-yl)ethylsuccinimidyl]nystatin $A_1$ (N11)

TLC $R_f$=0.19; UV-vis: $\lambda_{max}$ (MeOH) 319; 304; 291 nm; $E_1{}_{cm}^{1\%}$ (MeOH, $\lambda$=304 nm)=550 (theoretically for $C_{57}H_{89}N_3O_{19}$ is 653); MS-ESI calculated $C_{57}H_{89}N_3O_{19}$ [M+H]$^+$ 1120.3. found: 1120.6.

EXAMPLE 3

Synthesis of N-Thioureidyl Derivatives of Nystatin 200 mg (0.21 mmol) of Nystatin $A_1$ is dissolved in 4 ml of dimethyl formamide (DMF) in 100 ml round-bottomed flask equipped with a magnetic stirrer. The solution is cooled to 0° C. and 0.029 ml (0.21 mmol) of triethylamine (TEA) is slowly added. After 10 minutes 0.25 mmol of the appropriate isothiocyanate is added and the reaction mixture is warmed to room temperature. The reaction progress is monitored by thin layer chromatography (TLC) on Silica Gel (60 F254, Merck) in chloroform:methanol:water (10:6:1 v/v) solvent system. After then the reaction mixture is added dropwise to 150 ml of diethyl ether. The resulting, pale yellow precipitate, is filtered under reduced pressure on a Millipore funnel. The crude product is washed twice with diethyl ether (2×50 ml) and then dried in a vacuum desiccator. The residue is purified by column chromatography on normal phase, where the solid phase is Silica Gel and solvent system is chloroform:methanol (gradient from 20% to 55% of methanol). The fractions with pure product were collected and combined, then evaporated under reduced pressure at temperature not exceeding 35° C. Using in the reaction below indicated isothiocyanates, the following derivatives of Nystatin $A_1$ are obtained:

a) In the reaction with 2-(piperidin-1-yl)ethylisothiocyanate is obtained 50 mg of N-{3-[2-(piperidin-1-yl)ethyl]thioureidyl}nystatin $A_1$ (N12)

TLC $R_f$=0.32; UV-vis: $\lambda_{max}$ (MeOH) 319; 304; 291 nm; $E_1{}_{cm}^{1\%}$ (MeOH, $\lambda$=304 nm)=600 (theoretically for $C_{55}H_{89}N_3O_{17}S$ is 667); MS-ESI calculated for $C_{55}H_{89}N_3O_{17}S$ [M+H]$^+$ 1096.3; found: 1096.5.

b) In the reaction with 2-(morpholin-1-yl)ethylisothiocyanate is obtained 110 mg of N-{3-[2-(morpholin-1-yl)ethyl]thioureidyl}nystatin $A_1$(N13)

TLC $R_f$=0.2; UV-vis: $\lambda_{max}$ (MeOH) 319; 304; 291 nm; $E_1{}_{cm}^{1\%}$ (MeOH, $\lambda$=304 nm)=402 (theoretically for $C_{55}H_{89}N_3O_{18}S$ is 657); MS-ESI calculated for $C_{55}H_{89}N_3O_{18}S$ [M+H]$^+$ 1112.3; found: 1112.5.

c) In the reaction with N,N-diethyl-2-aminoethylisothiocyanate is obtained 20 mg of N-{3-[2-(N,N-diethylamino)ethyl]thioureidyl}nystatin $A_1$ (N14)

TLC $R_f$=0.12; UV-vis: $\lambda_{max}$ (MeOH) 319; 304; 291 nm; $E_1{}_{cm}^{1\%}$ (MeOH, $\lambda$=304 nm)=608 (theoretically for $C_{55}H_{91}N_3O_{17}S$ is 666); MS-ESI calculated for $C_{55}H_{91}N_3O_{17}S$ [M+H]$^+$ 1098.3; found: 1098.5.

d) In the reaction with 2-(4-methylpiperazin-1-yl)ethylisothiocyanate is obtained 50 mg of N-{3-[2-(4-methylpiperazin-1-yl)ethyl]thioureidyl}nystatin $A_1$ (N15)

TLC $R_f$=0.08; UV-vis: $\lambda_{max}$ (MeOH) 319; 304; 291 nm; $E_1{}_{cm}^{1\%}$ (MeOH, $\lambda$=304 nm)=662 (theoretically for $C_{55}H_{90}N_4O_{17}S$ is 658); MS-ESI calculated for $C_{55}H_{90}N_4O_{17}S$ [M+H]$^+$ 1111.3; found 1111.6.

e) In the reaction with z 2-(pyrrolidin-1-yl)ethylisothiocyanate is obtained 57 mg of N-{3-[2-(pyrrolidin-1-yl)ethyl]thioureidyl}nystatin $A_1$ (N16)

TLC $R_f$=0.26; UV-vis: $\lambda_{max}$ (MeOH) 319; 304; 291 nm; $E_1{}_{cm}^{1\%}$ (MeOH, $\lambda$=304 nm)=670 (theoretically for $C_{54}H_{87}N_3O_{17}S$ is 676); MS-ESI calculated for $C_{54}H_{87}N_3O_{17}S$ [M+H]$^+$ 1082.3; found 1082.1.

f) In the reaction with 3-(N,N-dimethylamino)propylisothiocyanate is obtained 44 mg of N-{3-[3-(N',N'-dimethylamino)propyl]thioureidyl}nystatin $A_1$ (N17)

TLC $R_f$=0.12; UV-vis: $\lambda_{max}$ (MeOH) 319; 304; 291 nm; $E_1{}_{cm}^{1\%}$ (MeOH, $\lambda$=304 nm)=641 (theoretically for $C_{53}H_{87}N_3O_{17}S$ is 683); MS-ESI calculated for $C_{53}H_{87}N_3O_{17}S$ [M+H]$^+$ 1070.3; found 1070.8.

g) In the reaction with 2-(N,N-dimethylamino)ethylisothiocyanate is obtained 53 mg of N-{3-[2-(N',N'-dimethylamino)ethyl]thioureidyl}nystatin $A_1$ (N18)

TLC $R_f$=0.19; UV-vis: $\lambda_{max}$ (MeOH) 319; 304; 291 nm; $E_1{}_{cm}^{1\%}$ (MeOH, $\lambda$=304 nm)=623 (theoretically for $C_{52}H_{85}N_3O_{17}S$ is 692); MS-ESI calculated for $C_{52}H_{85}N_3O_{17}S$ [M+H]$^+$ 1056.3; found 1055.9.

h) In the reaction with 3-(N,N-dimethylamino)-2,2-dimethylopropylisothiocyanate is obtained 124 mg of N-{3-[3-(N',N'-dimethylamino)-2,2-dimethylpropyl]thioureidyl}nystatin $A_1$ (N19)

TLC $R_f$=0.17; UV-vis $\lambda_{max}$ (MeOH) 319; 304; 291 nm, $E_1{}_{cm}^{1\%}$ (MeOH, $\lambda$=304 nm)=540 (theoretically for $C_{55}H_{91}N_3O_{17}S$ is 666); MS-ESI calculated for $C_{55}H_{91}N_3O_{17}S$ [M+H]$^+$ 1098.4; found 1098.2.

i) In the reaction with 3-(imidazo-1-yl)propylisothiocyanate is obtained 30 mg N-{3-[3-(imidazo-1-yl)propyl]thioureidyl}nystatin $A_1$ (N20)

TLC $R_f$=0.2; UV-vis: $\lambda_{max}$ (MeOH): 319; 304; 291 nm; $E_1{}_{cm}^{1\%}$ (MeOH, $\lambda$=304 nm)=560 (theoretically for $C_{54}H_{84}N_4O_{17}S$ is 669); MS-ESI calculated for $C_{54}H_{84}N_4O_{17}S$ [M+H]$^+$ 1093.3; found 1093.7.

EXAMPLE 4

Synthesis of N-Benzyl Derivatives of Nystatin $A_1$ 200 mg (0.21 mmol) of Nystatin $A_1$ is dissolved in 3 ml of dimethyl formamide (DMF) in 100 ml round-bottomed flask equipped with a magnetic stirrer. Next, 0.3 mmol of benzaldehyde is added and solution is stirred at room temperature for 1 hour. After 1 hour 3 ml of anhydrous methanol, 0.3 mmol of sodium cyanoborohydride and catalytic amount (0.015 ml) of acetic acid are added. The reaction progress is monitored by thin layer chromatography (TLC) on Silica Gel (60 F254, Merck) in chloroform:methanol:water (20:6:1 v/v) solvent system. The reaction mixture is cooled to −5° C., and then 0.015 ml of methylamine in tetrahydrofurane is added. The reaction mixture is left for 10 minutes and then added dropwise to 150 ml of diethyl ether. The resulting, pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform:methanol:water (20:6:1 v/v). The fractions with pure product were collected and combined, then evaporated under reduced pressure at temperature not exceeding 35° C. For example, in the reaction with benzaldehyde is obtained 55 mg of N-benzylnystatin A1 (N21).

TLC $R_f$=0.83; UV-vis: $\lambda_{max}$ (MeOH) 319; 304; 291 nm; $E_1{}_{cm}^{1\%}$ (MeOH, $\lambda$=304 nm)=420 (theoretically for $C_{54}H_{81}NO_{17}$ is 680); MS-ESI calculated for $C_{54}H_{81}NO_{17}$ [M−H]$^-$ 1114.6; found 1114.6.

EXAMPLE 5

Synthesis of N-Alkyl Derivatives of Nystatin 200 mg (0.21 mmol) of Nystatin $A_1$ is dissolved in 3 ml of dimethyl formamide (DMF) in 100 ml round-bottomed flask equipped with a magnetic stirrer. Next, 0.63 mmol of appropriate aliphatic aldehyde is added and solution is tirred at room temperature for 1 hour. After 1 hour 3 ml of anhydrous methanol, 0.63 mmol of sodium cyanoborohydride and catalytic amount of acetic acid (0,015 ml) are added. The reaction progress is monitored by thin layer chromatography (TLC) on Silica Gel (60 F254, Merck) in chloroform:methanol:water (10:6:1 v/v) solvent system. The reaction mixture is cooled at −5° C., and then 0,015 ml of methylamine in tetrahydrofurane is added. The reaction mixture is left for 10 minutes and then added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified on column chromatography on normal phase, where the solid phase is Silica Gel and solvent system is chloroform:methanol:water (10:6:1 v/v) or chloroform:methanol (gradient from 20% to 60% of methanol). The fractions with pure product were collected and combined, then evaporated under reduced pressure at temperature not exceeding 35° C. The following derivatives of Nystatin $A_1$ are obtained:

a) In the reaction with propanal is obtained 60 mg of N,N-di-n-propylnystatin $A_1$ (N22)

TLC $R_f$=0.35; UV-vis: $\lambda_{max}$ (MeOH) 319; 304; 291 nm; $E_1{}_{cm}^{1\%}$ (MeOH, $\lambda$=304 nm)=640 (theoretically for $C_{53}H_{87}NO_{17}$ is 659); MS-ESI calculated for $C_{53}H_{87}NO_{17}$ [M+H]$^+$ 1110.6; found: 1110.6.

b) In the reaction with methanal is obtained 90 mg N,N-dimethylnystatin $A_1$ (N23)

TLC $R_f$=0.18; UV-vis: $\lambda_{max}$ (MeOH) 319; 304; 291 nm; $E_1{}_{cm}^{1\%}$ (MeOH, $\lambda$=304 nm)=660 (theoretically for $C_{49}H_{79}NO_{17}$ is 766); MS-ESI calculated for $C_{49}H_{79}NO_{17}$ [M+H]$^+$ 954.7; found: 954.5.

c) In the reaction with ethanal is obtained 40 mg of N,N-diethylnystatin $A_1$ (N24)

TLC $R_f$=0.23; UV-vis: $\lambda_{max}$ (MeOH) 319; 304; 291 nm; $E_1{}_{cm}^{1\%}$ (MeOH, $\lambda$=304 nm)=570 (theoretically for $C_{51}H_{83}NO_{17}$ is 745); MS-ESI calculated for $C_{51}H_{83}NO_{17}$ [M+H]$^+$ 982.3; found: 982.5.

d) In the reaction with 3-(piperidin-1-yl)propanal is obtained N,N-di[3-(piperidin-1-yl) propyl]nystatin $A_1$ (N25)

TLC $R_f$=0.55; UV-vis: $\lambda_{max}$ (MeOH) 319; 304; 291 nm; $E_1{}_{cm}^{1\%}$ (MeOH, $\lambda$=304 nm)=540 (theoretically for $C_{63}H_{105}N_3O_{17}$ is 622); MS-ESI calculated for $C_{63}H_{105}N_3O_{17}$ [M+H]$^+$ 1177.4; found: 1177.5.

e) In the reaction with 3-(4-ethylpiperazin-1-yl)propanal is obtained N,N-di[3-(4-ethyl piperazin-1-yl)propyl]nystatin $A_1$ (N26)

TLC $R_f$=0.43; UV-vis: $\lambda_{max}$ (MeOH) 319; 304; 291 nm; $E_1{}_{cm}^{1\%}$ (MeOH, $\lambda$=304 nm)=520 (theoretically for $C_{63}H_{107}N_5O_{17}$ is 606); MS-ESI calculated for $C_{63}H_{107}N_5O_{17}$ [M+H]$^+$ 1207.5; found: 1207.8.

EXAMPLE 6

Synthesis of N-Alkyl Derivatives of N-Fructosylnystatin $A_1$ 200 mg (0.18 mmol) of N-fructosylnystatin $A_1$ is dissolved in 3 ml of dimethyl formamide (DMF) in 100 ml round-bottomed flask equipped with a magnetic stirrer. Next, 0.63 mmol of appropriate aliphatic aldehyde is added and solution is stirred at room temperature for 1 hour. After 1 hour 3 ml of anhydrous methanol, 0.63 mmol of sodium cyanoborohydride and catalytic amount of acetic acid (0.015 ml) are added. The reaction progress is monitored by thin layer chromatography (TLC) on Silica Gel (60 F254, Merck) in chloroform:methanol:water (7:6:1 v/v) or n-butanol:acetic acid:water (4:1:1 v/v) solvent system. The reaction mixture is cooled to −5° C., and then 0,015 ml (2M) of methylamine in tetrahydrofurane is added. The reaction mixture is left for 10 minutes and then is added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform:methanol:water (7:6:1 v/v). The fractions with pure product were collected and combined, then evaporated under reduced pressure at temperature not exceeding 35° C. The following derivatives of N-fructosylnystatin $A_1$ are obtained:

a) In the reaction with propanal is obtained 40 mg of N-fructosyl-N-n-propylnystatin $A_1$ (N27)

TLC $R_f$=0.15; UV-vis $\lambda_{max}$ (MeOH) 319; 304; 291 nm; $E_1{}_{cm}^{1\%}$ (MeOH, $\lambda$=304 nm)=590 (theoretically for $C_{56}H_{91}NO_{22}$ is 647); MS-ESI calculated for $C_{56}H_{91}NO_{22}$ [M+H]$^+$ 1130.6; found: 1131.0.

b) In the reaction with metanal is obtained 60 mg of N-fructosyl-N-methylnystatin $A_1$ (N28)

TLC $R_f$=0.16; UV-vis: $\lambda_{max}$ (MeOH) 319; 304; 291 nm; $E_1{}_{cm}^{1\%}$ (MeOH, $\lambda$=304 nm)=580 (theoretically for $C_{54}H_{87}NO_{22}$ is 664); MS-ESI calculated for $C_{54}H_{87}NO_{22}$ [M+H]$^+$ 1102.5; found: 1102.5.

c) In the reaction with ethanal is obtained 39 mg of N-fruktosyl-N-ethylnystatin $A_1$ (N29)

TLC $R_f$=0.18; UV-vis: $\lambda_{max}$ (MeOH) 319; 304; 291 nm; $E_1{}_{cm}^{1\%}$ (MeOH, $\lambda$=304 nm)=540 (theoretically for $C_{55}H_{89}NO_{22}$ is 655); MS-ESI calculated for $C_{55}H_{89}NO_{22}$ [M+H]$^+$ 1116.5; found: 1116.5.

d) In the reaction with 3-(N,N-dimethylamino)propanal is obtained N-fructosyl-N-[3-(N′,N′-dimethylamino)propyl]nystatin $A_1$ (N30)

TLC $R_f$=0.12; UV-vis: $\lambda_{max}$ (MeOH) 319; 304; 291 nm; $E_1{}_{cm}^{1\%}$ (MeOH, $\lambda$=304 nm)=550 (theoretically for $C_{58}H_{96}N_2O_{22}$ is 624); MS-ESI calculated for $C_{58}H_{96}N_2O_{22}$ [M+H]$^+$ 1174.5; found: 1174.7.

e) In the reaction with 3-(piperidin-1-yl)propanal is obtained N-fructosyl-N-[3-(piperidin-1-yl)propyl]nystatin $A_1$ (N31)

TLC $R_f$=0.17; UV-vis: $\lambda_{max}$ (MeOH) 319; 304; 291 nm; $E_1{}_{cm}^{1\%}$ (MeOH, $\lambda$=304 nm)=520 (theoretically for $C_{61}H_{100}N_2O_{22}$ is 603); MS-ESI calculated for $C_{61}H_{100}N_2O_{22}$ [M+H]$^+$ 1213.5; found: 1213.9.

f) In the reaction with 3-(4-ethylpiperazin-1-yl)propanal is obtained N-fructosyl-N-[3-(4-ethylpiperazin-1-yl)propyl]nystatin $A_1$ (N32)

TLC $R_f$=0.1; UV-vis: $\lambda_{max}$ (MeOH) 319; 304; 291 nm; $E_1{}_{cm}^{1\%}$ (MeOH, $\lambda$=304 nm)=510 (theoretically for $C_{61}H_{101}N_3O_{22}$ is 595); MS-ESI calculated for $C_{61}H_{101}N_3O_{22}$ [M+H]$^+$ 1229.5; found: 1229.9.

EXAMPLE 7

Synthesis of N-Aminoacyl and N—(N'-Alkylamino)Acyl Derivatives of Nystatin $A_1$ 0.26 mmol of N-(9-fluorenylomethoxycarbonyl)aminoacid (Fmoc-aminoacid), 0.26 mmol of N-hydroxysuccinimide (HONSu), 53 mg (0.26 mmol) of dicyclohexylcarbodiimide (DCC) is dissolved in 3 ml of dimethyl formamide (DMF) in 50 ml round-bottomed flask equipped with a magnetic stirrer. The reaction mixture is stirred at 37° C. for 1 hour. The reaction progress is monitored by thin layer chromatography (TLC) on Silica Gel (60 F254, Merck) in ethyl aceteate:hexan (7:3 v/v) solvent system. During the reaction, the precipitated N,N-dicyclohexylurea is filtered and washed with 1 ml of DMF. To the filtrate 200 mg (0.22 mmol) of Nystatin $A_1$ and 0.04 ml (0.22 mmol) of triethylamine (TEA) are added. Stirring is continued at 37° C. for 3 hours. After the reaction, another portion of 0.04 ml (0.22 mmol) of TEA is added and the reaction mixture is left for 2 hours at room temperature, and then added dropwise to 150 ml of diethyl ether. The resulting, pale yellow precipitate, is filtered under reduced pressure on a Millipore funnel. The crude product is washed twice with diethyl ether (2×50 ml) and then dried in a vacuum desiccators. The residue is purified on column chromatography on normal phase, where the solid phase is Silica Gel and solvent system is chloroform:methanol:water (15:8:1 v/v). The fractions with pure product were collected and combined, then evaporated under reduced pressure at temperature not exceeding 35° C. The following derivatives of Nystatin $A_1$ are obtained in the reaction of the corresponding protected amino acids:

a) In the reaction with N-Fmoc-D-phenylglycine is obtained 92 mg of N-D-phenylglycylnystatin $A_1$ (N33)

TLC $R_f$=0.38; UV-vis: $\lambda_{max}$ (MeOH) 319; 304; 291 nm; $E_1{}_{cm}^{1\%}$ (MeOH, $\lambda$=304 nm)=610 (theoretically for $C_{55}H_{82}N_2O_{18}$ is 691); MS-ESI calculated for $C_{55}H_{82}N_2O_{18}$ [M+H]$^+$: 1059.6; found: 1059.6.

b) In the reaction with N-Fmoc-L-phenylalanine is obtained 140 mg of N-L-phenylalanylnystatin $A_1$ (N34)

TLC $R_f$=0.42; UV-vis: $\lambda_{max}$ (MeOH) 319; 304; 291 nm; $E_1{}_{cm}^{1\%}$ (MeOH, $\lambda$=304 nm)=600 (theoretically for $C_{56}H_{84}N_2O_{18}$ is 681); MS-ESI calculated for $C_{56}H_{84}N_2O_{18}$ [M+H]$^+$ 1073.6; found: 1073.9.

c) In the reaction with N-Fmoc-L-(O-tert-butyl)glutamic acid is obtained 30 mg of N-L-(O-tert-butyl)glutamylnystatin $A_1$ (N35)

TLC $R_f$=0.26; UV-vis: $\lambda_{max}$ (MeOH) 319; 304; 291 nm; $E_1{}_{cm}^{1\%}$ (MeOH, $\lambda$=304 nm)=610 (theoretically for $C_{56}H_{90}N_2O_{20}$ is 658); MS-ESI calculated for $C_{56}H_{90}N_2O_{20}$ [M+H]$^+$ 1111.7; found 1112.0.

d) In the reaction with N-Fmoc-L-(O-tert-butyl)serine is obtained 80 mg of N-L-(O-tert-butyl)serylnystatin $A_1$ (N36)

TLC $R_f$=0.35; UV-vis: $\lambda_{max}$ (MeOH) 319; 304; 291 nm; $E_1{}_{cm}^{1\%}$ (MeOH, $\lambda$=304 nm)=610 (theoretically for $C_{54}H_{88}N_2O_{19}$ is 684); MS-ESI calculated for $C_{54}H_{88}N_2O_{19}$ [M+H]$^+$ 1069.6; found 1069.7.

e) In the reaction with N-Fmoc-D-(O-tert-butyl)glutamic acid is obtained 40 mg of N-D-(O-tert-butyl)glutamylnystatine $A_1$ (N37)

TLC $R_f$=0.26; UV-vis: $\lambda_{max}$ (MeOH) 319; 304; 291 nm; $E_1{}_{cm}^{1\%}$ (MeOH, $\lambda$=304 nm)=510 (theoretically for $C_{56}H_{90}N_2O_{20}$ is 658); MS-ESI calculated for $C_{56}H_{90}N_2O_{20}$ [M+H]$^+$ 1111.7; found 1112.

f) In the reaction with N-Fmoc-D-(O-tert-butyl)serine is obtained 95 mg of N-D-(O-tert-butyl)serylnystatin $A_1$ (N38)

TLC $R_f$=0.35; UV-vis: $\lambda_{max}$ (MeOH) 319; 304; 291 nm; $E_1{}_{cm}^{1\%}$ (MeOH, $\lambda$=304 nm)=540 (theoretically for $C_{54}H_{88}N_2O_{19}$ is 684); MS-ESI calculated for $C_{54}H_{88}N_2O_{19}$ [M+H]$^+$ 1069.6; found 1069.7.

g) In the reaction with N-Fmoc-D-β-(1-naphtyl)alanine is obtained 30 mg of N-D-β-(1-naphtyl)alanylnystatin $A_1$ (N39)

TLC $R_f$=0.41; UV-vis: $\lambda_{max}$ (MeOH) 319; 304; 291 nm; $E_1{}_{cm}^{1\%}$ (MeOH, $\lambda$=304 nm)=640 (theoretical for $C_{60}H_{86}N_2O_{18}$ is 651); MS-ESI calculated for $C_{60}H_{86}N_2O_{18}$ [M+H]$^+$ 1123.6; found 1124.3.

h) In the reaction with N-Fmoc-L-(4-nitrophenyl)alanine is obtained 56 mg of N-L-(4-nitrophenyl)alanylnystatin $A_1$ (N40)

TLC $R_f$=0.42; UV-vis: $\lambda_{max}$ (MeOH) 319; 304; 291 nm; $E_1{}_{cm}^{1\%}$ (MeOH, $\lambda$=304 nm)=560 (theoretically for $C_{56}H_{83}N_3O_{20}$ is 654); MS-ESI calculated for $C_{56}H_{83}N_3O_{20}$ [M+H]$^+$ 1118.6; found 1119.2.

i) In the reaction with N-Fmoc-D-(O-tert-butyl)asparagine is obtained 40 mg of N-D-(O-tert-butyl)asparagylnystatin $A_1$ (N41)

TLC $R_f$=0.35; UV-vis: $\lambda_{max}$ (MeOH) 319; 304; 291 nm; $E_1{}_{cm}^{1\%}$ (MeOH, $\lambda$=304 nm)=620 (theoretically $C_{55}H_{88}N_2O_{20}$ is 667); MS-ESI calculated for $C_{55}H_{88}N_2O_{20}$ [M+H]$^+$ 1097.7; found 1098.0.

j) In the reaction with N-Fmoc-D-β-(pyridin-3-yl)alanine is obtained 80 mg of N-D-β-(pyridin-3-yl)alanylnystatin $A_1$ (N42)

TLC $R_f$=0.37; UV-vis: $\lambda_{max}$ (MeOH) 319; 304; 291 nm; $E_1{}_{cm}^{1\%}$ (MeOH, $\lambda$=304 nm)=520 (theoretically for $C_{55}H_{83}N_3O_{18}$ is 681); MS-ESI calculated for $C_{55}H_{83}N_3O_{18}$ [M−H]$^-$ 1073; found 1072.9.

k) In the reaction with N-Fmoc-N-methyl-2-amino-2-methylpropanoic acid is obtained 50 mg of N-[2-(N-methylamino)-2-methylpropan]nystatin $A_1$ (N43)

TLC $R_f$=0.13; UV-vis: $\lambda_{max}$ (MeOH) 319; 304; 291 nm; $E_1{}_{cm}^{1\%}$ (MeOH, $\lambda$=304 nm)=610 (theoretically for $C_{52}H_{84}N_2O_{18}$ is 715); MS-ESI calculated for $C_{52}H_{84}N_2O_{18}$ [M−H]$^-$ 1023.6; found 1023.7.

EXAMPLE 8

Synthesis of N—(N',N'-Dialkylamino)Aminoacyl Derivatives of Nystatin $A_1$ 0.44 mmol of aminoacid, 0.44 mmol of N-hydroxysuccinimide (HONSu), 0.44 mmol (0.26 mmola) of dicyclohexylcarbodiimid (DCC) is dissolved in 3 ml of dimethyl formamide (DMF) in 50 ml round-bottomed flask equipped with a magnetic stirrer. The reaction mixture is stirred at 37° C. for 1 hour. The reaction progress is monitored by thin layer chromatography (TLC) on Silica Gel (60 F254, Merck) in ethyl acetate:hexane (7:3 v/v) solvent system. During the reaction precipitated N,N'-dicyclohexylurea is filtered and washed with 1 ml DMF. To the filtrate 200 mg (0.22 mmol) of Nystatin $A_1$ and 0.04 ml (0.22 mmol) of triethylamine are added. The reaction progress is monitored by thin layer chromatography (TLC) on Silica Gel (60 F254, Merck) in chloroform:methanol:water (10:6:1 v/v) solvent system. Stirring is continued at 37° C. for 6-16 hours. After then the reaction mixture is added dropwise to 150 ml of diethyl ether. The resulting pale yellow precipitate, is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform:methanol:water (10:6:1 v/v). The fractions containing pure product were collected and combined, then evaporated under reduced pressure at temperature not exceeding 35° C. The following derivatives of Nystatin $A_1$ are obtained in the reaction with the corresponding amino acids:

a) In the reaction with 3-(piperidin-1-yl)propionic acid is obtained 50 mg of N-[3-(piperidin-1-yl)propionyl]nystatin $A_1$ (N44)

TLC $R_f$=0.09; UV-vis: $\lambda_{max}$ (MeOH) 319; 304; 291 nm; $E_1{}_{cm}^{1\%}$ (MeOH, $\lambda$=304 nm)=680 (theoretically for $C_{55}H_{83}N_3O_{18}$ is 688); MS-ESI calculated for $C_{55}H_{88}N_2O_{18}$ [M–H]⁻: 1063.6; found 1063.4.

b) In the reaction with N,N-dimethyl-L-phenylalanine is obtained 110 mg of N—[L-(N,N-dimethylphenylalanyl] nystatin $A_1$ (N45)

TLC $R_f$=0.43; UV-vis: $\lambda_{max}$ (MeOH) 319; 304; 291; $E_1{}_{cm}^{1\%}$ (MeOH, $\lambda$=304 nm)=590 (theoretically for $C_{58}H_{88}N_2O_{18}$ is 664); MS-ESI calculated for $C_{58}H_{88}N_2O_{18}$ [M–H]⁻: 1101.6; found 1101.6.

EXAMPLE 9

Synthesis of Methyl Esters of N-Substituted Derivatives of Nystatin $A_1$ 0.1 mmol of Nystatin $A_1$ derivative is dissolved in a mixture of dimethyl formamide/methanol (3 ml/1 ml), next mixture was cooled to 0° C. and excess of diazomethane (ether solution) in a molar ratio of 2.5:1 is added. The reaction mixture is left for 2 hour at 0° C. The reaction progress is monitored by thin layer chromatography (TLC) on Silica Gel (60 F254, Merck) in chloroform:methanol:water (10:6:1 v/v) solvent system. After the reaction, the excess of diazomethane is decomposed with acetic acid, and the reaction mixture is added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform:methanol:water (15:6:1 v/v). The fractions containing product were collected and combined, then evaporated under reduced pressure at temperature not exceeding 35° C. In manner described above, exemplary is obtained 40 mg of N-fructosyl-N-n-propylnystatin $A_1$ methyl ester (N53)

TLC $R_f$=0.55; UV-vis $\lambda_{max}$ (MeOH) 319; 304; 291 nm; $E_1{}_{cm}^{1\%}$ (MeOH, $\lambda$=304 nm)=550 (theoretically for $C_{57}H_{93}NO_{22}$ is 639); MS-ESI calculated for $C_{57}H_{93}NO_{22}$ [M+H]⁺ 1144.6; found: 1145.0.

EXAMPLE 10

Synthesis of Amides of N-Substituted Derivatives of Nystatin $A_1$ 0.1 mmol of Nystatin $A_1$ derivative is dissolved in 5 ml of DMF in the round-bottomed flask equipped with a magnetic stirrer. The mixture was cooled to 0° C. and 1 mmol of 3-N,N-dimethylpropyldiamine, 1 mmol of diphenyl azidephosphate (DPPA), and 1 mmol TEA are added. The reaction mixture is left for 24 hours. The reaction progress is monitored by thin layer chromatography (TLC) on Silica Gel (60 F254, Merck) in chloroform:methanol:water (10:6:1 v/v) solvent system. The reaction mixture is added dropwise to 100 ml of diethyl ether. The resulting pale yellow precipitate, is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform:methanol:water (15:6:1 v/v). The fractions containing product were collected and combined, then evaporated under reduced pressure at temperature not exceeding 35° C. In manner described above, exemplary is obtained 25 mg of N-fructosyl-N-n-propylnystatin $A_1$ 3-(N',N'-dimethylamino) propylamide (N57).

TLC $R_f$=0.45; UV-vis $\lambda_{max}$ (MeOH) 319; 304; 291 nm; $E_1{}_{cm}^{1\%}$ (MeOH, $\lambda$=304 nm)=530 (teoretically for $C_{61}H_{103}N_3O_{21}$ is 603); MS-ESI calculated for $C_{61}H_{103}N_3O_{21}$ [M+H]⁺ 1213.6; found: 1213.0.

EXAMPLE 11

Preparation of Salts with N-Methyl-D-Glucamine of Amphoteric Nystatin $A_1$ Derivatives 0.1 mmol derivative of Nystatin $A_1$ in 2 ml of deionized water is suspended in round-bottomed flask equipped with a magnetic stirrer and then 0.11 mmol of N-methyl-D-glucamine dissolved in 1 ml of water is added. Next, to the solution excess of acetone is added. The resulting pale yellow precipitate is filtered under reduced pressure on a Millipore funnel. The crude product is twice washed with diethyl ether (2×50 ml) and then dried in a vacuum desiccator. In the manner described above exemplary is obtained 96 mg of N-methyl-D-glucamine salt of N-fructosyl-N-n-propylnystatin $A_1$ (N59).

UV-vis $\lambda_{max}$ (MeOH) 319; 304; 291 nm; $E_1{}_{cm}^{1\%}$ (MeOH, $\lambda$=304 nm)=530 (theoretically for $C_{63}H_{104}N_2O_{27}$ is 553).

EXAMPLE 12

Preparation of Salts with L-Aspartic Acids of Basic Derivatives of Nystatin $A_1$ 0.1 mmol derivative of Nystatin $A_1$ is suspended in 2 ml of deionized water in round-bottomed flask equipped with a magnetic stirrer. Next, to the reaction mixture 0.11 mmol of L-aspartic acid dissolved in 1 ml of water is added. The solution is filtered and to clear filtrate excess of acetone is added to precipitated. The resulting pale yellow precipitate, is filtered under reduced pressure on a Millipore funnel. The crude product is twice washed with diethyl ether (2×50 ml) and then dried in a vacuum desiccator. In the manner described above exemplary is obtained 105 mg of L-aspartate of N-methyl-N-n-fructosylpropylnystatin $A_1$ methyl ester (N60)

UV-vis $\lambda_{max}$ (MeOH) 319; 304; 291 nm; $E_{1\ cm}^{1\%}$ (MeOH, $\lambda$=304 nm)=510 (theoretically for $C_{61}H_{100}N_2O_{29}$ is 572).

EXAMPLE 13

Antifungal Activity In Vitro and Hemotoxicity of Nystatin $A_1$ Derivatives

For the determination of antifungal activity in vitro we used method of serial dilution in buffered medium RPMI 1640, pH 7.0, in a 96-wells microplates, according to the standard procedure (National Committee for Clinical Laboratory Standards. Reference method for broth dilution antifungal susceptibility testing of yeast, approved standard, 2nd ed. M27-A2 vol. 22 Wayne, Pa., 2002). The optical density of cells suspension was measured using a microplates reader (Victor³, Perkin-Elmer) at the wavelength $\lambda$=531 nm ($A_{531}$). On the basis of obtained results the diagrams of relation between $A_{531}$ values and concentration of examined compound were made. From these graphs, the $IC_{50}$ values were read, which were the interpolated concentrations of a tested compound, at which the $A_{531}$ value was exactly 50% of the $A_{531}$ value for the control sample. Moreover, MIC values, that are the lowest concentration of tested compound at which the $A_{531}$ value were at most 20% of the $A_{531}$ value measured for the control sample.

The hemotoxicity determination were carried out by the serial dilutions method, according to the procedure described earlier (Ślisz, M., et al., E., *J Antibiot* 57: 669-678 (2004)). Human erythrocytes were suspensed in the solution of saline to obtain a cell density of suspension $2\times10^7$/ml. Suitable amounts of diluted solutions of compounds were added to the cell suspension in tubes and were incubated at 37° C. for 30 minutes and then centrifuged (1700×g, 10 min, 4° C.). The concentration of hemoglobin in supernatant after centrifugation of erythrocytes suspension were determined by measuring the absorbance at wavelength $\lambda$=540 nm ($A_{540}$). The maximum level of hemolysis was obtained after incubation of cells suspension in the presence of 0.1% Tritone X-100 (control sample). On the basis of obtained results the diagrams on relation between the $A_{540}$ value and concentration of examined compound were made. From these graphs, the $EH_{50}$ values were read which are the interpolated concentrations of compound, for which the $A_{540}$ value is exactly 50% of the $A_{540}$ value measured for the control sample. Maximum concentrations of tested derivatives could not exceed 300 μg/ml, to maintain full solubility in experimental conditions. At this maximum concentration of compounds which exhibited especially low hemotoxicity, it was not possible to determine the $EH_{50}$ value. For this group of derivatives, additionally the value of $EH_{10}$ (the concentration causing 10% of hemolysis) was determined. In addition for the group of compounds of the lowest hemotoxiciy, % of hemolysis was determined at concentration of examined compound 300 μg/ml, and at concentration 60 μg/ml, at which Nystatin $A_1$ induces 100% hemolysis.

Obtained results are presented below in tables 2A, 2B, 2C and 2D.

TABLE 2A

Antifungal activity and hemotoxicity of compounds.

| | | Antifungal activity [μg ml⁻¹] | | | | | | |
|---|---|---|---|---|---|---|---|---|
| No | Symbol | *Saccharomyces cerevisiae* ATCC 9763 MIC | *Candida albicans* ATCC 10231 MIC | *Candida albicans* ATCC 10231 IC$_{50}$ | *Candida tropicalis* KKP 334 MIC | *Candida glabrata* DSM 11226 MIC | *Candida krusei* DSM 6128 MIC | *Candida lusitaniae* DSM 70102 MIC | Hemotoxicity [μg ml⁻¹] BEH$_{50}$ |
| 1. | Nys | 0.5 | 0.5 | 0.23 | 0.5 | 1 | 1 | 0.25 | 35.87 |
| 2. | N1 | 8 | 8 | 5.36 | 8 | 16 | 32 | nt | >300 |
| 3. | N2 | 8 | 8 | 4.99 | 8 | 16 | 16 | nt | >300 |
| 4. | N3 | 8 | 16 | 11.76 | 16 | 32 | Nt | nt | >300 |
| 5. | N4 | 8 | 8 | 6.32 | 8 | 16 | 16 | nt | >300 |
| 6. | N5 | 8 | 8 | 5.77 | 8 | 16 | 16 | nt | >300 |
| 7. | N6 | 8 | 8 | 5.52 | 8 | 16 | 16 | 4 | >300 |
| 8. | N7 | 8 | 8 | 3.99 | 8 | 8 | 16 | 4 | >300 |
| 9. | N8 | 2 | 2 | 1.54 | 2 | 4 | 4 | 2 | 175.29 |
| 10. | N9 | 8 | 8 | 5.62 | 8 | 16 | 16 | 4 | >300 |
| 11. | N10 | 8 | 8 | 5.47 | 8 | 16 | 16 | 4 | >300 |
| 12. | N11 | 8 | 8 | 3.91 | 8 | 8 | 8 | 4 | >150 |
| 13. | N12 | 8 | 8 | 4.20 | 8 | 8 | 16 | 4 | >300 |
| 14. | N13 | 8 | 8 | 3.88 | 8 | 16 | 16 | 8 | >300 |
| 15. | N14 | 4 | 8 | 3.21 | 8 | 16 | 16 | 4 | >150 |
| 16. | N15 | 8 | 8 | 5.74 | 8 | 16 | 16 | 4 | >300 |
| 17. | N16 | 4 | 4 | 3.04 | 4 | 8 | 8 | 4 | 146.19 |
| 18. | N17 | 4 | 4 | 2.92 | 4 | 8 | 8 | 4 | 257.05 |
| 19. | N18 | 4 | 4 | 2.97 | 4 | 8 | 8 | 4 | 133.37 |
| 20. | N19 | 4 | 4 | 2.90 | 4 | 8 | 8 | 4 | 280.47 |
| 21. | N20 | 8 | 8 | 6.47 | 8 | 16 | 16 | 8 | >200 |
| 22. | N21 | 2 | 4 | 2.32 | 4 | 4 | 4 | nt | 188.56 |
| 23. | N22 | 2 | 4 | 3.14 | 4 | 4 | 8 | nt | 280.41 |
| 24. | N23 | 4 | 4 | 2.47 | 4 | 8 | 8 | 2 | 282.63 |
| 25. | N24 | 8 | 8 | 3.82 | 8 | 16 | 16 | 4 | >300 |
| 26. | N28 | 4 | 8 | 5.80 | 8 | 16 | 16 | nt | >250 |
| 27. | N29 | 8 | 8 | 3.56 | 8 | 16 | 16 | 8 | >300 |
| 28. | N30 | 8 | 8 | 5.79 | 16 | 16 | 16 | 8 | >300 |
| 29. | N34 | 4 | 8 | 6.01 | 8 | 8 | 8 | nt | >300 |
| 30. | N35 | 8 | 8 | 6.36 | 16 | 16 | 16 | nt | >300 |
| 31. | N37 | 4 | 4 | 2.73 | 4 | 8 | 8 | nt | >300 |

TABLE 2A-continued

Antifungal activity and hemotoxicity of compounds.

| | | Antifungal activity [μg ml$^{-1}$] | | | | | | | |
|---|---|---|---|---|---|---|---|---|---|
| | | Saccharomyces cerevisiae ATCC 9763 | Candida albicans ATCC 10231 | | Candida tropicalis KKP 334 | Candida glabrata DSM 11226 | Candida krusei DSM 6128 | Candida lusitaniae DSM 70102 | Hemotoxicity [μg ml$^{-1}$] |
| No | Symbol | MIC | MIC | IC$_{50}$ | MIC | MIC | MIC | MIC | BEH$_{50}$ |
| 32. | N38 | 8 | 8 | 5.95 | 8 | 16 | 16 | nt | >300 |
| 33. | N39 | 8 | 8 | 6.05 | 8 | 16 | 16 | nt | >300 |
| 34. | N40 | 8 | 8 | 5.56 | 8 | 16 | 16 | nt | >300 |
| 35. | N41 | 4 | 8 | 4.69 | 4 | 8 | 8 | nt | >300 |
| 36. | N42 | 8 | 16 | 10.54 | 16 | 32 | 32 | nt | >300 |
| 37. | N43 | 8 | 8 | 5.46 | 8 | 8 | 16 | nt | >300 |
| 38. | N44 | 4 | 4 | 2.95 | 4 | 8 | 8 | nt | >300 |
| 39. | N45 | 2 | 4 | 2.83 | 4 | 4 | 8 | nt | 236.19 |
| 40. | N46 | 4 | 4 | 2.83 | 4 | 8 | 8 | nt | >300 |

TABLE 2B

Antifungal activity of selected Nystatin A$_1$ derivatives and reference fluconazole.

| | MIC [μg/ml] | | | | | | | | | |
|---|---|---|---|---|---|---|---|---|---|---|
| Strain | Fluconazole | Nystatin | N19 | N22 | N28 | N33 | N37 | N41 | N45 | N46 |
| Candida albicans ATCC 10231 | 2 | 0.5 | 4 | 4 | 8 | 8 | 4 | 8 | 4 | 4 |
| Candida pseudotropicalis KKP 324 | 0.5 | 1 | 4 | 4 | 8 | 8 | 8 | 4 | 4 | 16 |
| Candida stellatoidea CBS 1905 | 0.5 | 1 | 8 | 4 | 8 | 8 | 8 | 4 | 4 | 8 |
| Candida parapsilosis DSM 5784 | 8 | 1 | 4 | 8 | 16 | 32 | 16 | 8 | 4 | 32 |
| Candida dubliniensis CBS 7987 | 2 | 1 | 4 | 2 | 8 | 16 | 8 | 2 | 2 | 16 |
| Candida quilliermondii DSM 11947 | 8 | 0.5 | 4 | 8 | 16 | 16 | 16 | 8 | 4 | 32 |
| Candida arborea KKP 319 | 8 | 1 | 4 | 8 | 32 | 32 | 32 | 8 | 8 | 32 |
| Candida lipolytica KKP 322 | 8 | 0.5 | 4 | 4 | 8 | 16 | 16 | 8 | 8 | 16 |
| Saccharomyces cerevisiae ATCC 9763 | 2 | 0.5 | 4 | 2 | 4 | 4 | 4 | 4 | 2 | 4 |
| Aspergillus niger LOCK E201 | 16 | 1 | 8 | 8 | 16 | 32 | 16 | 8 | 8 | 32 |
| Trichoderma viride LOCK E159 | 8 | 1 | 8 | 8 | 16 | 32 | 32 | 32 | 16 | 16 |

TABLE 2C

Hemotoxicity of selected compounds at 300 μg ml$^{-1}$

| No | Symbol | EH$_{10}$ [μg ml$^{-1}$] | % of hemolysis at the concentration 300 μg ml$^{-1}$ |
|---|---|---|---|
| 1. | Nys | 22.13 | 100 |
| 2. | N8 | 150.73 | |
| 3. | N17 | 156.33 | |
| 4. | N19 | 209.91 | |
| 5. | N21 | 91.60 | |
| 6. | N22 | 202.34 | |
| 7. | N23 | 214.20 | |
| 8. | N27 | >300 | 7.34 |
| 9. | N33 | >300 | 8.69 |
| 10. | N36 | >300 | 8.24 |
| 11. | N40 | >300 | 7.45 |
| 12. | N43 | 283.84 | |
| 13. | N44 | 209.39 | |
| 14. | N45 | >300 | 7.11 |

TABLE 2D

Hemotoxicity of selected compounds at 60 μg ml$^{-1}$

| No | Symbol | % of hemolysis at the concentration 60 μg ml$^{-1}$ |
|---|---|---|
| 1. | Nys | 100 |
| 2. | N28 | 0.17 |
| 3. | N34 | 0.02 |
| 4. | N37 | 0.04 |
| 5. | N41 | 0.15 |
| 6. | N44 | 0.95 |
| 7. | N46 | 0.37 |

EXAMPLE 14

Antifungal Activity in vitro of Nystatin A$_1$ Derivatives Against Multidrug Resistant (MDR) Fungal Strains The determination of antifungal activity was performed by the serial dilutions method in buffered RPMI 1640 medium, in a 96-wells microplates, according to the standard procedure (National Committee for Clinical Laboratory Standards. Reference method for broth dilution antifungal susceptibility testing of yeast, approved standard, 2nd ed. M27-A2 vol. 22 Wayne, Pa., 2002). The optical density of cells suspension was measured using a microplates reader (Victor$^3$, Perkin-Elmer) at the wavelength λ=660 nm (A$_{660}$). On the basis of received results the diagrams on interrelation between the A$_{660}$ value and the concentration of tested compound were made. From these graphs MIC values were read, that are the concentrations of tested compounds, in the presence at which $A_{660}$ value is at most 20% of $A_{660}$ value measured in control sample.

The results are presented in table 3.

added and absorption of solutions was measured at the wavelength $\lambda=540$ nm ($A_{540}$), using a microplates reader (Victor³, Perkin-Wallac). On the basis of received results the diagrams on the relation between the $A_{540}$ value and con-

TABLE 3

Antifungal activity of compounds towards resistant strains.

| Candida albicans | MIC [µg/ml] | | | | | | | | | |
|---|---|---|---|---|---|---|---|---|---|---|
| | Fluconazole | Nystatin | N19 | N22 | N28 | N33 | N37 | N41 | N45 | N46 |
| B3 | 0.5 | 0.5 | 4 | 8 | 8 | 4 | 8 | 8 | 4 | 8 |
| B4 | 16 | 1 | 4 | 8 | 8 | 8 | 8 | 16 | 4 | 8 |
| Gu4 | 0.5 | 0.5 | 4 | 8 | 8 | 8 | 8 | 8 | 4 | 8 |
| Gu5 | 256 | 1 | 4 | 8 | 16 | 8 | 8 | 8 | 4 | 16 |
| F2 | 32 | 1 | 4 | 4 | 8 | 16 | 16 | 16 | 8 | 16 |
| F5 | 128 | 1 | 4 | 4 | 16 | 32 | 16 | 16 | 8 | 16 |
| 5674 | 2048 | 1 | 4 | 4 | 16 | 16 | 32 | 16 | 8 | 32 |
| STY7 | 512 | 1 | 4 | 4 | 16 | 16 | 32 | 16 | 8 | 32 |
| STY19 | 64 | 1 | 4 | 4 | 16 | 16 | 32 | 0.5 | 4 | 32 |
| STY31 | 64 | 1 | 4 | 4 | 16 | 16 | 32 | 16 | 8 | 32 |

| Strains | Description | Reference |
|---|---|---|
| | Candida albicans clinical isolates | |
| B3 | fluconazole sensitive, parent strain for B4 | 1 |
| B4 | fluconazole-resistant due to the overexpression of CaMDR1 | 1 |
| Gu4 | fluconazole sensitive, parent strain for Gu5 | 1 |
| Gu5 | fluconazole-resistant due to the overexpression of CDR1 and CDR2 | 1 |
| F2 | fluconazole sensitive, parent strain for F5 | 2 |
| F5 | fluconazole-resistant due to the overexpression of CaMDR1 and ERG11 | 2 |
| STY7 | C. albicans 5674 overexpressing CDR1 and CDR2 mutant derivative, deletion of CDR2 | 3 |
| STY19 | C. albicans 5674 overexpressing CDR1 and CDR2 mutant derivative, deletion of CDR1 | 3 |
| STY31 | C. albicans 5674 overexpressing CDR1 and CDR2 mutant derivative, deletion of CDR1 and CDR2 | 3 |

1. Franz, R., Ruhnke M, Morschhäuser J. 1999 Molecular aspects of fluconazole resistance development in Candida albicans. Mycoses, 42, 453-458.
2. Franz, R., Kelly S. L., Lamb D. C., Kelly D. E., Ruhnke M., Morschhäuser J. 1998. Multiple molecular mechanisms contribute to a stepwise development of fluconazole resistance in Clinical Candida albicans strains. Antimicrobial Agents and Chemotherapy 42: 3065-3072.
3. Tsao S., Rahkhoodaee F., Raymond M. 2009. Relative contributions of the Candida albicansABC transporters Cdr1p and Cdr2p to clinical azole resistance. Antimicrobial Agents and Chemotherapy 53: 1344-1352.

EXAMPLE 15

Cytotoxic Activity of Nystatin $A_1$ Derivatives Against Mammalian Cells in Tissue Culture For examinations were used selected cell lines: CCRF-CEM—human acute lymphoblastic leukemia; HepG2—human malignant hepatoma; LLC-PK1—epithelial cell of pig kidney; All lines were from ATCC collection.

The study are conducted using described below methods of culturing and determination of cytotoxic activity.

CCRF-CEM cells were cultured in medium RPMI 1640+10% fetal bovine serum (FBS), LLC-PK1 cells in medium Medium 199+3% FBS, HepG2 cells in medium MEM+10% FBS. All media contained 100 µg/ml of penicillin G and streptomycin. 24-wells microplates containing appropriate medium were inoculated with the cells in amount of $1.2 \times 10^4$ cells/well and allowed to stand overnight. Next, tested compounds as solution in dimethylsulfoxide (DMSO) were added in volume of 10 µl (serial 2× dilutions). To control well 10 µl of DMSO was added. Microplates with cell suspensions were incubated for 120 h at temperature 37° C. at atmosphere of 95%/5% $CO_2$. After incubation, to all wells 200 µl of solution of 3-(4,5-dimethylthiazole-2-yl)-2,5-diphenylotetrazole bromide (MTT) in PBS (4 mg/ml) was added and plates were further incubated for 4 h at 37° C. Next, to dissolve crystals of formazane 1 ml of DMSO was centration of examined compound were prepared. From these graphs $IC_{50}$ values were read, that is concentration of tested compound in the presence at which $A_{540}$ value is half of $A_{540}$ value measured in the control sample.

The obtained results are presented in Table 4.

TABLE 4

Cytotoxicity of compounds towards mammalian cells.

| | $IC_{50}$ [µg/ml] | | |
|---|---|---|---|
| Compound | HepG2 | LLC-PK1 | CCRF-CEM |
| Nystatin | 24.9 ± 2.332 | >100 | >100 |
| N14 | >100 | >100 | >100 |
| N17 | >100 | >100 | >100 |
| N19 | >100 | >100 | >100 |
| N21 | 68.3 ± 8.06 | >100 | 91.9 ± 4.35 |
| N22 | 82.9 ± 19.87 | >100 | >100 |
| N28 | >100 | >100 | >100 |
| N34 | >100 | nt | >100 |
| N37 | >100 | 85.5 ± 4.30 | >100 |
| N39 | >100 | >100 | >100 |
| N41 | >100 | >100 | >100 |
| N44 | >100 | >100 | >100 |
| N45 | >100 | >100 | >100 |
| N46 | >100 | >100 | >100 |

The invention claimed is:

1. A compound of Formula 1a

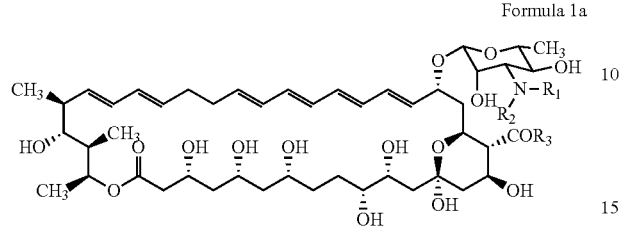

Formula 1a or a salt, hydrate or complex thereof;
wherein R$_1$ selected from the group consisting of:
- a) alkyl substituted with an optionally substituted alkylamino or an optionally substituted N-linked heterocycle;
- b) a succinimidyl derivative;
- c) an optionally substituted thioureidyl residue;
- d) an aminoacyl residue of structure:

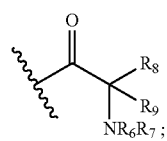

wherein R$_6$ and R$_7$ are independently chosen from a hydrogen atom or an optionally substituted alkyl, or R$_6$ and R$_7$ can be taken, together with the atom to which they are joined, to form an optionally substituted nitrogen-containing cyclic moiety; one of R$_8$ and R$_9$ is —U—V, wherein U is an optionally substituted alkyl linker or a single bond and V is an optionally substituted carbocyclic, heterocyclic, alkoxy, or ester moiety, and the other of R$_8$ and R$_9$ is hydrogen, or —U—V, wherein U is an optionally substituted alkyl linker or a single bond and V is a hydrogen atom, or an optionally substituted aliphatic, carbocyclic, heterocyclic, alkoxy, or ester moiety; and e) an aminoacyl of structure:

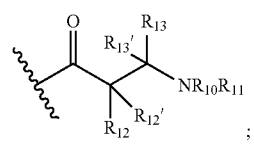

wherein R$_{10}$ and R$_{11}$ can be taken, together with the atom to which they are joined, to form an optionally substituted nitrogen-containing cyclic moiety; R$_{12}$ and R$_{13}$ are, independently, hydrogen or —U—V, wherein U is an optionally substituted alkyl linker or a single bond and V is a hydrogen atom, or an optionally substituted aliphatic, carbocyclic, heterocyclic, alkoxy, or ester moiety; and R$_{12'}$ and R$_{13'}$ are, independently, hydrogen or alkyl;

R$_2$ is a hydrogen atom, optionally substituted alkyl, a succinimidyl derivative, a glycosyl residue, an optionally substituted aminoacyl residue, or an optionally substituted thioureidyl residue;

R$_3$ is a hydroxyl group, alkoxyl group or an alkylamino or aminoalkyl derivative.

2. A compound according to claim 1, of Formula 1b

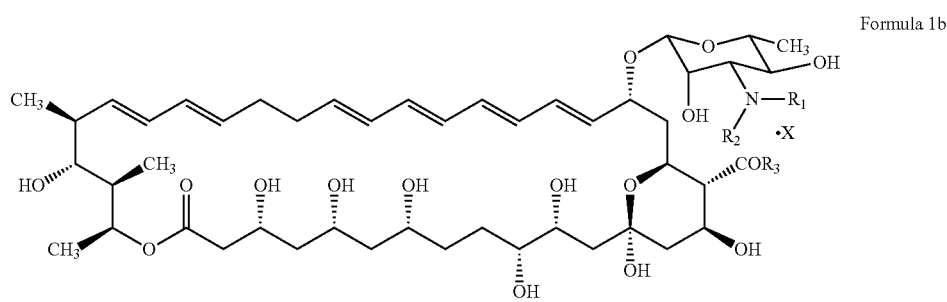

Formula 1b or a salt or complex thereof;

X is absent or present and, when present, X is one or more molecules of base or acid, or complexing compound.

3. The compound of claim 1, wherein, when one or both of $R_1$ and $R_2$ is, independently, selected from the group consisting of:

a) dialkylamino, or an optionally substituted N-linked heterocycle;

b) a succinimidyl derivative of structure

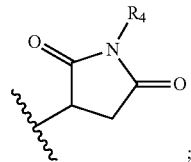

wherein $R_4$ is —X—Y, wherein X is an optionally substituted alkyl linker or a single bond; and Y is an optionally substituted carbo- or heterocyclic moiety or —NR*$_2$, —NH$_2$, or —NHR*, where R* is an optionally substituted aliphatic, an optionally substituted carbo- or heterocyclic moiety or two R* form, together with the nitrogen atom to which they are bound, an optionally substituted heterocycle;

c) a thioureidyl residue of structure

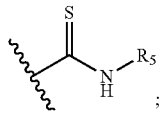

wherein $R_5$ is —W—Z, wherein W is an optionally substituted alkyl linker; and Z is an optionally substituted nitrogen-containing heterocycle, NR*$_2$, NH$_2$, or NHR*, where R* is an optionally substituted aliphatic, an optionally substituted carbo- or heterocyclic moiety, or two R* form, together with the nitrogen atom to which they are bound, an optionally substituted heterocycle;

d) an aminoacyl residue of structure:

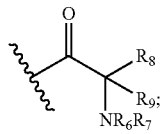

wherein $R_6$ and $R_7$ are independently chosen from a hydrogen atom or an optionally substituted alkyl, or $R_6$ and $R_7$ can be taken, together with the atom to which they are joined, to form an optionally substituted nitrogen-containing cyclic moiety; one of $R_8$ and $R_9$ is hydrogen and the other of $R_8$ and $R_9$ is —U—V, wherein U is an optionally substituted alkyl linker or a single bond and V is a hydrogen atom, or an optionally substituted carbocyclic, heterocyclic, alkoxy, or ester moiety; and e) an aminoacyl of structure:

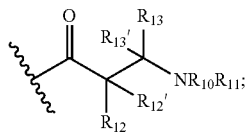

wherein $R_{10}$ and $R_{11}$ can be taken, together with the atom to which they are joined, to form an optionally substituted nitrogen-containing cyclic moiety; $R_{12}$ and $R_{13}$ are, independently, hydrogen or —U—V, wherein U is an optionally substituted alkyl linker or a single bond and V is a hydrogen atom, or an optionally substituted aliphatic, carbocyclic, heterocyclic, alkoxy, or ester moiety; and $R_{12'}$ and $R_{13'}$ are, independently, hydrogen or alkyl.

4. The compound according to claim 3, wherein Y is an optionally substituted carbo- or heterocyclic moiety or a dialkylamino.

5. The compound according to claim 1, wherein $R_2$ is a hydrogen atom, an unsubstituted non-branched alkyl or a substituted alkyl.

6. The compound according to claim 1, wherein $R_3$ is hydroxyl, methoxy, or —NR$_{14}$—(C$_1$-C$_6$alkyl)-NR$_{15}$R$_{16}$, wherein $R_{14}$ is a hydrogen atom or methyl, and $R_{15}$ and $R_{16}$ are independently selected from the group consisting of hydrogen and optionally substituted aliphatic.

7. A compound according to claim 1, selected from the group consisting of: N-(N'-benzylsuccinimidyl)nystatin $A_1$, N-(N'-4-bromophenylsuccinimidyl)nystatin $A_1$, N-(N'-2,4,6-trimethylphenylsuccinimidyl) nystatin $A_1$, N-(N'-2,6-dimethyl-phenylsuccinimidyl)nystatin $A_1$, N-(N'-cyclohexyl succinimidyl)nystatin $A_1$, N-[N'-3-(N'',N''-dimethylamino) propylsuccinimidyl]nystatin $A_1$, N-[N'-2-(N'',N''-dimethylamino)ethylsuccinimidyl]nystatin $A_1$, N-[N'-2-(piperidin-1-yl)ethylsuccinimidyl] nystatin $A_1$, N-[N'-2-(4-methylpiperazin-1-yl)ethylsuccinimidyl]nystatin $A_1$, N-[N'-3-(N'',N''-dimethylamino)-2,2-dimethylpropylosuccinimidyl]nystatin $A_1$ and N-[N'-2-(pyrrolidin-1-yl)ethylsuccinimidyl]nystatin $A_1$ or a salt, hydrate or complex thereof.

8. A compound according to claim 1, selected from the group consisting of: N-{3-[2-(piperidin-1-yl)ethyl] thioureidyl}nystatin $A_1$, N-{3-[2-(mopholin-1-yl)ethyl] thioureidyl}nystatin $A_1$, N-{3-[2-(N',N'-diethyl amino) ethyl]thioureidyl}nystatin $A_1$, N-{3-[2-(4-methylpiperazin-1-yl)ethyl]thioureidyl} nystatin $A_1$, N-{3-[2-(pyrrolidin-1-yl)ethyl]thioureidyl}nystatin $A_1$, N-{3-[3-(N',N'-dimethyl amino)propyl]thioureidyl}nystatin $A_1$, N-{3-[2-(N,N -dimethylamine)ethyl]thioureidyl}nystatin $A_1$, N-{3-[3-(N',N'-dimethylamine)-2,2-dimethylpropyl]thioureidyl}nystatin $A_1$ and N-{3-[3-(imidazole-1-yl)propyl]thioureidyl}nystatin $A_1$ or a salt, hydrate or complex thereof.

9. A compound according to claim 1, selected from the group consisting of: N,N-di[3-(piperidin-1-yl)propyl]nystatin $A_1$ or N,N-di[3-(4-ethylpiperazin-1-yl)propyl]nystatin $A_1$, N-fructosyl-N-[3-(N',N'-dimethylamine)propyl]nystatin $A_1$, N-fructosyl-N-[3-(piperidin-1'-yl)propyl]nystatin $A_1$, and N-fructosyl-N-[3-(4-ethylpiperazin-1-yl) propyl)]nystatin $A_1$, or a salt, hydrate or complex thereof.

10. A compound selected from the group consisting of: N-benzylnystatin $A_1$, N,N-di-n-propylnystatin $A_1$, N,N-dimethylnystatin $A_1$, N,N-diethylnystatin $A_1$, N,N-di-n-propylnystatin $A_1$ methyl ester, N-fructosyl-N-n-propylnystatin A₁ methyl ester, 3-(N',N'-dimethyl-amino)propylamide of N'',N''-di-n-propylonystatin A₁, 3-(N',N'-dimethylamino)propylamide of N-fructosyl-N-n-propylnystatin A1, N-[2-(N-methylamino)-2-methylpropyl]nystatin A₁, N-[(N',N'-di-n-propyl)glycyl]nystatin A₁, N-[3-(N',N'-di-n-propylamino)propionyl]nystatin A₁, N-[3-(N,N-diethyl-amino)propionyl] nystatin A₁, and N-[3-(N,N-dimethylamino)propionyl] nystatin A₁ or a salt, hydrate or complex thereof.

11. A compound, according to claim 1, selected from the group consisting of: N-D-phenyl-glycylnystatin A₁, N-L-phenylalanylnystatin A₁, N-L-(O-tert-butyl) glutamylnystatin A₁, N-L-(O-tert-butyl)serylnystatin A₁, N-D-(O-tert-butyl)glutamylnystatin A₁, N-D-(O-tert-butyl)serylnystatin A₁, N-D-β-naphtylalanylnystatin A₁, N-L-(4-nitrophenyl)alanylnystatin A₁, N-D-(O-tert-butyl)asparagylnystatin A₁, N-D-β-(pyridin-3-yl)alanylnystatin A₁ N-[3-(piperidin-1-yl)propionyl]nystatin A₁, N-[L-(N',N'-dimethyl) phenylalanyl]nystatinA₁, and N-[L-(N',N'-diethyl)phenylalanyl]nystatin A₁ or a salt, hydrate or complex thereof.

12. A compound according to claim 1, selected from the group consisting of:
N-{3-[3-(N',N'-dimethylamino)-2,2-dimethylpropyl]thioureidyl}nystatin A₁ methyl ester, N-D-phenylglycylnystatin A₁ methyl ester, 3-(N',N'-dimethylamino)propylamide of N-{3-[3-(N'',N''-dimethylamino)-2,3-dimethylpropyl]thioureidyl}nystatin A₁ and 3-(N,N-dimethylamino)propylamide of N-D-pheynylglycylnystatin A₁ or a salt, hydrate or complex thereof.

13. A compound according to claim 1, in form of a salt with an inorganic or organic base or an inorganic or organic acid.

14. A compound according to claim 1, in form of a complex with an inorganic or organic complexing compound.

15. A pharmaceutical composition comprising a compound of claim 1.

16. A method for treating fungal infection in a patient comprising administering to the patient a therapeutically effective amount of a compound according to claim 1, wherein the patient is a human or animal.

17. A method of treating fungal infection in a plant, comprising administering a composition comprising a compound of claim 1 to the plant.

18. A method of treatment as claimed in claim 16 or 17 wherein the fungal infection is caused by a strain of the genus *Candida*.

* * * * *